US009782590B2

(12) United States Patent
O'Connell et al.

(10) Patent No.: US 9,782,590 B2
(45) Date of Patent: Oct. 10, 2017

(54) BRAIN STIMULATION SYSTEM INCLUDING DIAGNOSTIC TOOL

(71) Applicant: Functional Neuromodulation Inc., Toronto (CA)

(72) Inventors: Dan O'Connell, Earlysville, VA (US); Todd Langevin, Edina, MN (US); Donald E. Reymers, Brevard, NC (US); J. Christopher Flaherty, Auburndale, FL (US)

(73) Assignee: Functional Neuromodulation, Inc. (CA)

( * ) Notice: Subject to any disclaimer, the term of this patent is extended or adjusted under 35 U.S.C. 154(b) by 0 days.

(21) Appl. No.: 14/917,917

(22) PCT Filed: Oct. 16, 2014

(86) PCT No.: PCT/IB2014/003188
§ 371 (c)(1),
(2) Date: Apr. 8, 2016

(87) PCT Pub. No.: WO2015/079324
PCT Pub. Date: Jun. 4, 2015

(65) Prior Publication Data
US 2016/0220821 A1 Aug. 4, 2016

Related U.S. Application Data

(60) Provisional application No. 61/893,023, filed on Oct. 18, 2013.

(51) Int. Cl.
*A61N 1/36* (2006.01)
*A61N 2/00* (2006.01)
(Continued)

(52) U.S. Cl.
CPC ........ *A61N 1/36139* (2013.01); *A61B 5/0402* (2013.01); *A61B 5/0476* (2013.01);
(Continued)

(58) Field of Classification Search
CPC ......... A61N 1/37241; A61N 1/3605–1/36096; A61N 1/36139; A61N 1/36146; A61B 5/4088
See application file for complete search history.

(56) References Cited

U.S. PATENT DOCUMENTS 5,782,798 A 7/1998 Rise
6,227,203 B1 5/2001 Rise et al.
(Continued)

FOREIGN PATENT DOCUMENTS

WO WO 2011133583 A1 * 10/2011 ......... A61N 1/36082

OTHER PUBLICATIONS

International search report and written opinion dated Jul. 10, 2015 for PCT/IB2014/003188.

*Primary Examiner* — Tammie K Heller
(74) *Attorney, Agent, or Firm* — Wilson Sonsini Goodrich & Rosati

(57) ABSTRACT

A system for treating a patient comprises a stimulator for stimulating brain tissue, a controller for setting stimulation parameters and a diagnostic tool for measuring patient parameters and producing diagnostic data. The stimulation parameters comprise test stimulation parameters and treatment stimulation parameters. The stimulator delivers test stimulation energy to the brain tissue based on at least one test stimulation parameter and delivers treatment stimulation energy to the brain tissue based on at least one treatment stimulation parameter. One or more treatment stimulator parameters are determined based on the diagnostic data produced by the diagnostic tool The system is constructed (Continued)

and arranged to treat a neurological disease or a neurological disorder. Methods of treating a neurological disease or neurological disorder are also provided.

18 Claims, 4 Drawing Sheets

(51) Int. Cl.
*A61N 5/06* (2006.01)
*A61M 5/172* (2006.01)
*A61B 5/00* (2006.01)
*A61M 5/142* (2006.01)
*A61B 5/0402* (2006.01)
*A61B 5/0476* (2006.01)
*A61B 5/055* (2006.01)
*A61N 1/372* (2006.01)
*A61N 1/05* (2006.01)
*A61N 7/00* (2006.01)

(52) U.S. Cl.
CPC ............ *A61B 5/055* (2013.01); *A61B 5/4088* (2013.01); *A61M 5/14276* (2013.01); *A61M 5/1723* (2013.01); *A61N 1/0534* (2013.01); *A61N 1/36025* (2013.01); *A61N 1/36064* (2013.01); *A61N 1/36067* (2013.01); *A61N 1/36082* (2013.01); *A61N 1/36096* (2013.01); *A61N 1/37241* (2013.01); *A61N 2/006* (2013.01); *A61N 5/0622* (2013.01); *A61N 1/0531* (2013.01); *A61N 1/36017* (2013.01); *A61N 1/36153* (2013.01); *A61N 1/36171* (2013.01); *A61N 1/36175* (2013.01); *A61N 5/0601* (2013.01); *A61N 2005/0626* (2013.01); *A61N 2007/0026* (2013.01)

(56) References Cited

U.S. PATENT DOCUMENTS

| | | | |
|---|---|---|---|
| 7,087,008 B2 | 8/2006 | Fox et al. | |
| 8,000,795 B2 | 8/2011 | Lozano | |
| 8,078,275 B2 | 12/2011 | Lozano | |
| 8,612,006 B2 | 12/2013 | Lozano et al. | |
| 8,892,200 B2 | 11/2014 | Wagner et al. | |
| 2006/0212090 A1 | 9/2006 | Lozano et al. | |
| 2007/0060974 A1 | 3/2007 | Lozano | |
| 2007/0067001 A1 | 3/2007 | Lozano et al. | |
| 2007/0067002 A1 | 3/2007 | Lozano | |
| 2011/0275963 A1 | 11/2011 | Wagner et al. | |
| 2013/0289385 A1 | 10/2013 | Lozano et al. | |

\* cited by examiner

BRAIN STIMULATION SYSTEM INCLUDING DIAGNOSTIC TOOL

CROSS-REFERENCE TO RELATED APPLICATIONS

This application is a continuation of International Patent Application No. PCT/IB2014/003188 filed Oct. 16, 2014, which claims priority under 35 USC 119(3) to U.S. Provisional Patent Application Ser. No. 61/893,023, entitled "Brain Stimulation System including Diagnostic Tool", filed Oct. 18, 2013, the contents of which are incorporated herein by reference in their entirety.

This application is related to: U.S. patent Ser. No. 11/303,293, now U.S. Pat. No. 8,000,795, entitled "Cognitive Function within a Human Brain", filed Dec. 16, 2005; U.S. patent application Ser. No. 11/303,292, now U.S. Pat. No. 8,612,006, entitled "Inducing Neurogenesis within a Human Brain", filed Dec. 16, 2005; U.S. patent Ser. No. 11/303,619, now U.S. Pat. No. 8,078,275, entitled "Regulation of Neurotrophins", filed Dec. 16, 2005; U.S. patent application Ser. No. 11/365,977, now abandoned, entitled "Method of Treating Cognitive Disorders Using Neuromodulation", filed Mar. 1, 2006; and U.S. patent application Ser. No. 13/655,652, now abandoned, entitled "Deep Brain Stimulation of Memory Circuits in Alzheimer's Disease", filed Oct. 19, 2012; the contents of which are each incorporated herein by reference in their entirety.

FIELD OF INVENTION

The present invention relates generally to methods and systems for treating a neurological disease or disorder, such as Alzheimer's Disease or other cognitive disorder. In particular, a system includes a stimulation device and a diagnostic tool used to set one or more treatment stimulation parameters used to treat a neurological disease or disorder.

BACKGROUND OF THE INVENTION

Brain stimulation has been performed to treat numerous patient diseases and disorders, such as neurological and psychiatric conditions. Both invasive and non-invasive technologies have been developed. One non-invasive system includes a transcranial magnetic stimulation device that directs a magnetic field from outside the patient's head to induce electric currents in the patient's brain. Deep brain stimulation (DBS) can be accomplished using surgically implanted electrodes that deliver electrical stimulation to precisely targeted areas in the brain. More than 60,000 patients have been implanted with deep brain electrodes, and its predominant application has been in the treatment of movement disorders, most commonly Parkinson's disease.

There is a need for enhanced DBS and other brain stimulation systems, device and methods that result in increased safety and improved efficacy in the treatment of patients.

SUMMARY

According to an aspect of the present inventive concepts, a system for treating a patient comprises a stimulator for stimulating brain tissue, a controller and at least one diagnostic tool. The system is constructed and arranged to treat at least one of a neurological disease or a neurological disorder. The controller is configured to set one or more stimulation parameters comprising at least one test stimulation parameter of the stimulator and at least one treatment stimulation parameter of the stimulator. The diagnostic tool is configured to measure at least one patient parameter and produce diagnostic data representing the at least one measured patient parameter. The stimulator is constructed and arranged to deliver test stimulation energy to the brain tissue based on the at least one test stimulation parameter and to deliver treatment stimulation energy to the brain tissue based on the at least one treatment stimulation parameter. The at least one treatment stimulation parameter is determined based on the diagnostic data.

In some embodiments, the system is constructed and arranged to determine the treatment stimulation parameter to at least one of prevent or reduce an adverse event.

In some embodiments, the system is constructed and arranged to determine the treatment stimulation parameter to improve the treatment of the at least one of a neurological disease or a neurological disorder.

In some embodiments, the at least one treatment stimulation parameter comprises the at least one test stimulation parameter.

In some embodiments, the setting of the at least one treatment stimulation parameter comprises at least one of setting an initial treatment stimulation parameter or modifying an existing treatment stimulation parameter.

In some embodiments, the stimulator is constructed and arranged to stimulate brain tissue with a first set of test stimulation parameters for a first time period and a second set of test stimulation parameters for a second time period, and the diagnostic data can comprise first diagnostic data associated with the first stimulation time period and second diagnostic data associated with the second time period. The at least one treatment stimulation parameter can approximate the first set of test stimulation parameters or the second set of test stimulation parameters. The at least one treatment stimulation parameter can be associated with a desired treatment of the at least one of a neurological disease or a neurological disorder. The at least one treatment stimulation parameter can be associated with a desired memory recall by the patient. The at least one treatment stimulation parameter can be associated with at least one of prevention or reduction of an adverse event. The adverse event can comprise an event selected from the group consisting of: undesirable heart rate; undesirable respiration rate; undesirable sweating; undesirable hallucinations; undesirable tingling; flushing; undesirable psychiatric effect; undesirable cognitive effect; unpleasant generalized warming; undesirable perceptions described as déjà vu; seizure; synchronized neuronal firing pattern; undesired neural response time; undesired brain state; undesired theta phase; undesired p300 amplitude; and combinations thereof. The first time period and the second time period can comprise approximately the same length of time. At least one of the first time period or the second time period can comprise a time period of less than or equal to 24 hours, such as a time period of less than or equal to 6 hours, 3 hours, 1 hour, 30 minutes, 15 minutes, 10 minutes, 5 minutes or 2 minutes. The diagnostic tool can comprise a memory test device. The memory test device can comprise a form for recording memory test data. The at least one treatment stimulation parameter can approximate the set of test stimulation parameters that resulted in a higher test score. The diagnostic tool can comprise a diagnostic device. At least one of the first set of test stimulation parameters or the second set of test stimulation parameters can be determined based on diagnostic data produced by the diagnostic tool.

In some embodiments, at least one of the stimulation parameters comprises an electrical stimulation parameter selected from the group consisting of: voltage level such as an average voltage level, root mean square (rms) voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; and combinations thereof.

In some embodiments, the stimulator comprises a brain inserted lead comprising multiple electrodes, and at least one of the stimulation parameters comprises a subset of electrodes that receive stimulating energy. The subset of electrodes can comprise a single electrode. The subset of electrodes can comprise a pair of electrodes.

In some embodiments, at least one of the stimulation parameters comprises a signal voltage ranging between 0.1 Volts and 10.0 Volts. The at least one stimulation parameter can comprise a signal voltage ranging between 1.0 Volts and 6.0 Volts, such as a voltage between 1.0 Volts and 3.0 Volts. The at least one stimulation parameter can comprise a voltage of less than or equal to 9.0 Volts, such as a stimulation parameter comprising a voltage of less than or equal to 8.0 Volts, 7.0 Volts, 6.0 Volts, 5.0 Volts, 4.0 Volts or 3.5 Volts.

In some embodiments, at least one of the stimulation parameters comprises a signal frequency ranging between 2 Hz and 1000 Hz. The at least one stimulation parameter can comprise a signal frequency of approximately 130 Hz.

In some embodiments, at least one test stimulation parameter comprises a signal pulse width ranging between 30 microseconds and 150 microseconds. The at least one test stimulation parameter can comprise a signal pulse width of approximately 90 microseconds.

In some embodiments, at least one of the stimulation parameters comprises a light stimulation parameter selected from the group consisting of: power of light delivered to tissue; frequency of light delivered to tissue; a modulation parameter of light delivered to tissue; and combinations thereof.

In some embodiments, at least one of the stimulation parameters comprises a sound stimulation parameter selected from the group consisting of: amplitude of sound delivered to tissue; frequency of sound delivered to tissue; a modulation parameter of sound delivered to tissue; and combinations thereof.

In some embodiments, at least one of the stimulation parameters comprises an agent delivery stimulation parameter selected from the group consisting of: mass of agent delivered to tissue; volume of agent delivered to tissue; concentration of agent delivered to tissue; delivery rate of agent delivered to tissue; and combinations thereof.

In some embodiments, the controller is constructed and arranged to set at least one stimulation parameter based on a threshold at which an adverse event is detected by the diagnostic tool. The adverse event can comprise an event selected from the group consisting of: undesirable heart rate; undesirable respiration rate; undesirable sweating; undesirable hallucinations; undesirable tingling; flushing; undesirable psychiatric effect; undesirable cognitive effect; unpleasant generalized warming; undesirable perceptions described as déjà vu; seizure; synchronized neuronal firing pattern; undesired neural response time; undesired brain state; undesired theta phase; undesired p300 amplitude; and combinations thereof. The at least one stimulation parameter can be set using a safety margin, such as a safety margin of at least 10%, or at least 20%, 30%, 40% or 50%. The at least one stimulation parameter set based on the adverse event threshold can comprise the at least one treatment stimulation parameter. The at least one stimulation parameter set based on the adverse event threshold can comprise the at least one test stimulation parameter.

In some embodiments, the controller is constructed and arranged to set at least one stimulation parameter based on a threshold at which a desired event was detected by the diagnostic tool. The desired event can comprise an event selected from the group consisting of: recall of a desired memory; achievement of desired memory learning; desired level of neuronal activity; acceptable physiologic condition such as an acceptable heart rate or acceptable level of neuronal activity; experiential phenomena such as those described in epilepsy literature; and combinations thereof. The at least one stimulation parameter set based on the desired event threshold can comprise the at least one treatment stimulation parameter. The at least one stimulation parameter set based on the desired event threshold can comprise the at least one test stimulation parameter.

In some embodiments, the system is constructed and arranged to provide open loop stimulation.

In some embodiments, the system is constructed and arranged to provide closed loop stimulation. The closed loop stimulation can be provided based on the diagnostic data produced by the diagnostic tool. The system can further comprise a sensor for producing a signal, wherein the closed loop stimulation is provided based on the sensor signal.

In some embodiments, the measuring performed by the diagnostic tool comprises a function selected from the group consisting of: recording; gathering; assessing; collecting; determining; processing; combining; and combinations thereof.

In some embodiments, the diagnostic tool is constructed and arranged to detect an adverse event. The adverse event can comprise an event selected from the group consisting of: undesirable heart rate; undesirable respiration rate; undesirable sweating; undesirable hallucinations; undesirable tingling; flushing; undesirable psychiatric effect; undesirable cognitive effect; unpleasant generalized warming; undesirable perceptions described as déjà vu; seizure; synchronized neuronal firing pattern; undesired neural response time; undesired brain state; undesired theta phase; undesired p300 amplitude; and combinations thereof.

In some embodiments, the diagnostic tool comprises a device selected from the group consisting of: heart rate monitor; EKG measurement device; oximeter; combined heart rate and oximeter device such as a pulse oximeter; blood pressure measurement device; neuronal activity measurement device; EEG measurement device; evoked response potential (ERP) measurement device; neurochemical analysis device; memory test device; memory test form; respiration measurement device; sweat measurement device; skin conductivity measurement device; pH measurement device; body motion measurement device; imaging device; and combinations thereof.

In some embodiments, the diagnostic tool comprises at least two devices selected from the group consisting of: heart rate monitor; EKG measurement device; oximeter; combined heart rate and oximeter device such as a pulse oximeter; blood pressure measurement device; neuronal activity measurement device; EEG measurement device; evoked response potential (ERP) measurement device; neurochemical analysis device; memory test device; memory test form; respiration measurement device; sweat measurement device; skin conductivity measurement device; pH measurement device; body motion measurement device; imaging device; and combinations thereof. The diagnostic tool can comprise at least a heart rate monitor and a blood pressure measurement device. The diagnostic tool can be constructed and arranged to detect a patient issue. The patient issue can comprise an inaccurate representation made by the patient detected by at least one of heart rate data or blood pressure data.

In some embodiments, the diagnostic tool comprises an EKG measurement device. At least one stimulation parameter can be set based on detection of undesired EKG activity by the diagnostic tool.

In some embodiments, the diagnostic tool comprises a neuronal activity measurement device. The neuronal activity measurement device can be constructed and arranged to measure a neuronal parameter selected from the group consisting of: single neuron activity; local field potential; event related potentials; electroencephalogram readings; electrocorticogram readings; and combinations thereof. At least one stimulation parameter can be set based on the detection of a condition selected from the group consisting of: seizure; synchronized neuronal firing pattern; undesired neural response time; undesired brain state; undesired theta phase; undesired p300 amplitude; and combinations thereof.

In some embodiments, the diagnostic tool comprises an ERP measurement device. At least one stimulation parameter can be set based on the detection of undesired ERP activity by the diagnostic tool.

In some embodiments, the diagnostic tool comprises a blood pressure measurement device. At least one stimulation parameter can be set based on the detection of an undesired blood pressure reading by the diagnostic tool.

In some embodiments, the diagnostic tool comprises a blood oxygen measurement device. At least one stimulation parameter can be set based on the detection of an undesired blood oxygen reading by the diagnostic tool.

In some embodiments, the diagnostic tool comprises a body motion measurement device. At least one stimulation parameter can be set based on the detection of an undesired body motion detected by the diagnostic tool. The undesired body motion can comprise a tremor.

In some embodiments, the diagnostic tool comprises a neurochemical analysis device. The neurochemical analysis device can be constructed and arranged to measure a patient parameter selected from the group consisting of: a neurotransmitter level; a pH concentration; an ion concentration; a lactate level; cerebral blood flow; glucose utilization; oxygen extraction; and combinations thereof. At least one stimulation parameter can be set based on the detection of at least one of an undesired neurochemical activity or an undesired neurochemical level.

In some embodiments, the diagnostic tool comprises an imaging device. The stimulator can comprise multiple stimulating elements and at least one stimulation parameter can comprise at least one stimulating element selected to deliver stimulation energy. The stimulator can comprise multiple stimulating electrodes and at least one stimulation parameter can comprise at least one stimulating electrode selected to deliver electrical stimulation energy. The at least one stimulating electrode can be selected based on its position relative to tissue to be stimulated. The tissue to be stimulated can comprise at least the fornix.

In some embodiments, the diagnostic tool comprises an algorithm for analyzing a patient assessment.

In some embodiments, the diagnostic tool comprises a patient assessment recording tool. The patient assessment recording tool can comprise a tool selected from the group consisting of: form; a paper form; electronic form; tablet; personal computer; database; and combinations thereof. The patient assessment can comprise an assessment selected from the group consisting of: an assessment received verbally from the patient; an assessment received in written form from the patient; an assessment made by a caregiver of the patient; and combinations thereof. The patient assessment can comprise an assessment of the patient state selected from the group consisting of: depression; paranoia; schizophrenia; suicidality; suicide ideation; apathy; anxiety; mania; and combinations thereof.

In some embodiments, the diagnostic tool comprises a sensor constructed and arranged to sense, record or otherwise produce the diagnostic data. The sensor can comprise at least one sensing element selected from the group consisting of: neuronal activity sensor; EEG sensor; local field potential sensor; neurochemical sensor; pH sensor; pressure sensor; blood pressure sensor; an optical sensor; blood gas sensor; blood oxygen sensor; a magnetic sensor; a strain gauge; and combinations thereof. The sensor can comprise an implanted sensor. The sensor can be further constructed and arranged to stimulate brain tissue. The sensor can comprise at least one electrode.

In some embodiments, at least a first portion of the stimulator is constructed and arranged to be implanted in the patient and the system can be constructed and arranged to collect the diagnostic data after implantation of the stimulator first portion. The diagnostic data can be collected at least 5 minutes after implantation of the stimulator first portion, such as at least 24 hours or at least two weeks after implantation of the stimulator first portion.

In some embodiments, the system further comprises a stimulation threshold, and the at least one treatment stimulation parameter is set based on the stimulation threshold. The at least one treatment stimulation can be set using a safety margin.

In some embodiments, the system further comprises a stimulation threshold, and the at least one treatment stimulation parameter is modified based on the stimulation threshold. The at least one treatment stimulation parameter can be modified using a safety margin.

In some embodiments, the at least one of a neurological disease or disorder comprises a disease or disorder selected from the group consisting of: Alzheimer's Disease (AD) such as Mild or Moderate Alzheimer's Disease; probable Alzheimer's Disease; a genetic form of Alzheimer's Disease; Mild Cognitive Impairment (MCI); hippocampal damage such as hippocampal damage due to Alzheimer's disease, anoxia, epilepsy or depression; neuronal loss; neuronal damage; chemotherapy induced memory impairment; epilepsy; a seizure disorder; dementia; amnesia; a memory disorder such a spatial memory disorder; cognitive impairment associated with Schizophrenia; Parkinson's Disease related cognitive impairment or dementia; and combinations thereof.

In some embodiments, the system is constructed and arranged to treat at least one of: negative symptoms of schizophrenia; negative symptoms of depression; a condition of reversible impaired memory; or a condition of reversible impaired cognition.

In some embodiments, the system is constructed and arranged to treat at least one neurological disease and at least one neurological disorder. In some embodiments, the system is constructed and arranged to treat multiple neurological diseases. In some embodiments, the system is constructed and arranged to treat multiple neurological disorders. In some embodiments, the system is constructed and arranged to regulate the level of one or more neurotrophic factors and/or neurotransmitters. In some embodiments, the system is constructed and arranged to ameliorate cognitive decline associated with dementia.

In some embodiments, the patient has reduced integrity of white matter tracts innervating limbic structures such as the fornix as determined by fractional anisotropy maps using diffusion tensor imaging. The innervated limbic structures can comprise at least the fornix.

In some embodiments, the system is constructed and arranged to achieve at least one of: treats memory impairment; improves memory function; treats cognitive function loss; reverses synaptic loss; improves cognitive function; reduces degradation of cognitive function; promotes neurogenesis in the hippocampus of the patient's brain; drives neurotrophin expression; regulates one or more biomarkers related to Alzheimer's Disease such as amyloid-beta, tau, and/or phosphorylated tau; regulates BDNF expression; increases neurotransmitter release such as acetylcholine; or improves glucose utilization in the temporal lobe, the parietal lobe or both lobes of the patient's brain.

In some embodiments, the brain tissue stimulated comprises tissue selected from the group consisting of: fornix; entorhinal cortex; hippocampus; anterior thalamic nucleus; amygdala; mammillary bodies; parahippocampal cortex; temporal neocortex; septal nuclei; nucleus basalis of Meynert; subcallosal or subgenual cingulate; ventral capsule; ventral striatum and combinations thereof. In some embodiments, the brain tissue stimulated comprises brain tissue selected from the group consisting of: Papez Circuit; hippocampus; cingulate gyrus; fornix; a mammilothalamic tract; amygdala; hypothalamus; mammillary bodies; septal nuclei; temporal neocortex; the medial forebrain bundle; anterior and mediodorsal nuclei of the thalamus; the diagonal band of the Broca; temporal stem and temporal white matter; brainstem; nucleus basalis of Meynert; anterior thalamic nucleus; entorhinal cortex; rhinal cortex; periventricular zone; anterior thalamus; anterior insula; caudate; dorsal anterior cortex; dorsal cingulate; medial frontal cortex; nucleus accumbens; orbital frontal cortex; parietal region; periaqueductal gray area; posterior cingulate area; subcallosal area; subcallosal cingulate; subgenual cingulate; Brodmann area 10; Brodmann area 24; Brodmann area 25; Brodmann area 11/Brodmann area 10; Brodmann area 24*b*; Brodmann area 31; Brodmann area 32/Brodmann area 10; Brodmann area 32/Brodmann area 11; Brodmann area 39; Brodmann area 46; Brodmann area 46/Brodmann area 9; Brodmann area 47; Brodmann area 6; Brodmann area 9; ventral/medial prefrontal cortex area; ventral/medial white matter; dorsolateral prefrontal cortex; premotor cortex; ventrolateral prefrontal cortex; dorsal anterior cingulate caudate nucleus; frontal pole periaqueductal gray area; dorsolateral prefrontal area; subsingular cingulate; parahippocampal cortex; parahippocampal gyrus; ventral capsule; ventral striatum; and combinations thereof. In some embodiments, the brain tissue stimulated does not comprise tissue selected from the group consisting of: hippocampal tissue; optical tract tissue; and combinations thereof. In some embodiments, the brain tissue stimulated does not comprise tissue selected from the group consisting of: posterior hypothalamic area; ventral tegmental area; lateral hypothalamic area; anterior hypothalamic nucleus; paraventricular nucleus; dorsal medial hypothalamic nucleus; ventromedial hypothalamic nucleus; arcuate nucleus; lateral tuberal nucleus; medial preoptic nucleus; supraoptic nucleus; and combinations thereof.

In some embodiments, the stimulator comprises at least an implanted portion. The at least an implanted portion can comprise at least one electrode constructed and arranged to stimulate brain tissue. The at least one electrode can comprise an electrode selected from the group consisting of: single component bipolar electrode; multiple unipolar electrodes; stacked contact electrodes; discrete electrodes, an electrode strip, a grid of electrodes; paddle electrode; high-density/high channel or lead count micro-electrodes; and combinations thereof. The at least one electrode can comprise at least one electrode positioned in brain tissue. The at least one electrode can comprise at least one electrode positioned proximate the fornix. The at least one electrode can comprise two electrodes constructed and arranged to be placed bilaterally about the fornix. The at least one electrode can comprise at least one electrode positioned in a location to cause stimulation of the fornix. The at least one electrode can comprise multiple electrodes. The at least one electrode can comprise an electrode constructed and arranged for monopolar delivery of electrical energy. The at least one electrode can comprise an electrode constructed and arranged for multipolar delivery of electrical energy. The at least an implanted portion can comprise an implanted stimulation element selected from the group consisting of: electrode such as one or more electrodes configured to deliver electrical stimulation energy; magnetic field delivery element; light delivery element such as a visible, ultraviolet or infrared light delivery element; optogenetic delivery element; sound delivery element such as a subsonic wave or ultrasound wave delivery element; agent delivery element such as a chemical or pharmaceutical agent delivery element; and combinations thereof. The system can further comprise an energy generating element constructed and arranged to deliver energy selected from the group consisting of: electromagnetic energy such as electrical energy and/or or magnetic energy; light energy such as visible, ultraviolet and/or infrared light energy; sound energy such as subsonic, sonic or ultrasound energy; and combinations thereof. The at least an implanted portion can comprise an implanted signal generator.

In some embodiments, the stimulator comprises at least an external portion. The at least an external portion can comprise an external stimulation element. The external stimulation element can comprise an electromagnetic field generator. The external stimulation element can comprise a sound generator. The external stimulation element can comprise a light energy generator. The at least an external portion can comprise an electrical signal generator. The stimulator can further comprise an implanted stimulation element electrically connected to the electrical signal generator. The implanted stimulation element can comprise at least one electrode.

In some embodiments, the stimulator comprises an implanted portion and an external portion.

In some embodiments, the stimulator is constructed and arranged to stimulate tissue with electrical stimulation.

In some embodiments, the stimulator is constructed and arranged to stimulate tissue with a stimulation energy selected from the group consisting of: electrical stimulation; magnetic stimulation; optical stimulation such as visible, ultraviolet or infrared light stimulation; sound stimulation such as ultrasound or subsonic wave stimulation; chemical stimulation such as stimulation from a drug or other agent; and combinations thereof.

In some embodiments, the stimulator is constructed and arranged to stimulate the brain tissue in a continuous stimulation mode. In some embodiments, the stimulator is constructed and arranged to stimulate the brain tissue in a cyclical stimulation mode.

In some embodiments, the stimulator is further constructed and arranged to stimulate non-brain tissue. The non-brain tissue can comprise non-brain nerve tissue. The non-brain tissue can comprise non-brain organ tissue. The non-brain tissue can comprise tissue selected from the group consisting of: vagus nerve; trigeminal nerve; carotid sinus; spinal cord; dorsal root ganglia; tibial nerve; sacral nerve; gastric nerve; and combinations thereof.

In some embodiments, the stimulator comprises at least a portion of the diagnostic tool.

In some embodiments, the stimulator comprises at least one sensor.

In some embodiments, the controller is constructed and arranged to transmit information to the stimulator via wireless communication.

In some embodiments, the controller comprises at least a portion of the diagnostic tool.

In some embodiments, the controller comprises an algorithm for analyzing the diagnostic data produced by the diagnostic tool. The algorithm can be constructed and arranged to compare the diagnostic data to a threshold. The algorithm can be constructed and arranged to set the at least one treatment stimulation parameter based on a safety margin.

According to another aspect of the present inventive concepts, a method for treating a patient comprises selecting a patient and providing a stimulation system. The stimulation system comprises a stimulator; a controller; and a diagnostic tool. The method further includes measuring at least one patient parameter with the diagnostic tool and producing diagnostic data representing the at least one measured patient parameter; and setting a stimulation parameter of the system with the controller based on the diagnostic data. The method is constructed and arranged to treat at least one of a neurological disease or a neurological disorder.

In some embodiments, the system, stimulator, controller and/or diagnostic tool are constructed and arranged as described hereabove.

In some embodiments, the method further comprises implanting at least a portion of the stimulator in the patient. The method can further comprise performing an MRI procedure prior to and/or during the stimulator implantation to produce at least one MRI image, wherein the stimulator comprises a stimulating element that is implanted relative to a fornix target identified on the at least one MRI image Implanting the stimulator can comprise implanting one or more electrodes in a location selected from the group consisting of: in the Papez Circuit of the patient's brain; approximately 2 mm anterior and parallel to the vertical portion of the fornix; in the optic tract such that the ventralmost contact is 2 mm above the dorsal surface of the optic tract; approximately 5 mm from the midline; and combinations thereof.

In some embodiments, the stimulation parameter set comprises a treatment stimulation parameter.

In some embodiments, the stimulation parameter set comprises a test stimulation parameter.

In some embodiments, the stimulation parameter is set using a safety margin.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

DETAILED DESCRIPTION OF THE DRAWINGS

Figure 1:
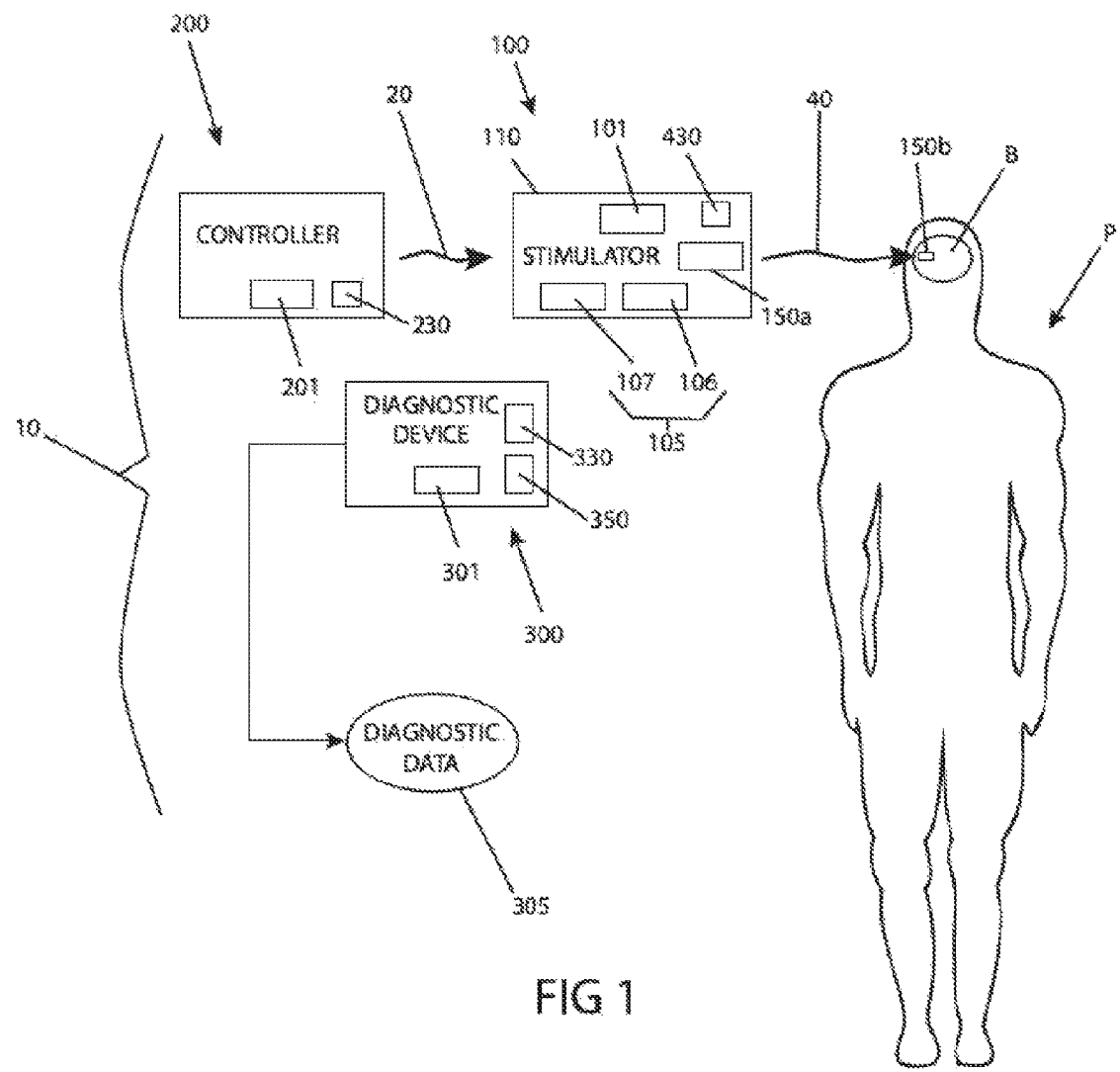
FIG. 1 illustrates a schematic view of a system for stimulating one or more portions of a patient's brain, consistent with the present inventive concepts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element or intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

For example, it will be appreciated that all features set out in any of the claims (whether independent or dependent) can be combined in any given way.

The systems, devices and methods of the present inventive concepts are applicable to treat a patient, such as to treat one or more cognitive disorders of a patient. The cognitive disorders include but are not limited to Alzheimer's Disease (AD) such as Mild or Moderate Alzheimer's Disease; probable Alzheimer's Disease; a genetic form of Alzheimer's Disease; Mild Cognitive Impairment (MCI); hippocampal damage such as hippocampal damage due to Alzheimer's disease, anoxia, epilepsy or depression; neuronal loss; neuronal damage; chemotherapy induced memory impairment; epilepsy; a seizure disorder; dementia; amnesia; a memory disorder such a spatial memory disorder; cognitive impairment associated with Schizophrenia; Parkinson's Disease related cognitive impairment or dementia; and combinations of these. Additionally or alternatively, the patient can be selected to treat negative symptoms of a disease or disorder selected from the group consisting of: schizophrenia; depression; other conditions of reversible impaired memory or cognition; and combinations of these.

In some embodiments, the patient is selected for treatment as described in applicant's co-pending U.S. application Ser. No. 13/655,652, entitled "Deep Brain Stimulation of Memory Circuits in Alzheimer's Disease", filed Oct. 19, 2012, the contents of which is incorporated herein by reference in its entirety.

As used herein, the term "wired pathway" shall refer to an energy and/or information transmission pathway including a physical conduit such as a flexible conduit comprising: one or more wires; one or more optical (e.g. light transmitting) fibers; one or more fluid delivery tubes; and combinations of these.

As used herein, the term "wireless" or "wireless pathway" shall refer to an energy and/or information transmission pathway that does not include or otherwise rely on a physical conduit for transmission, such as an electromagnetic or light transmission of energy and/or information that passes through the tissue of a patient without the use of a physical conduit.

Referring now to FIG. 1, a system for stimulating a patient's brain is illustrated, consistent with the present inventive concepts. System 10 includes stimulator 100, controller 200 and diagnostic tool 300. System 10 can be constructed and arranged to treat a neurological disease, a neurological disorder and/or another patient disease or disorder, as described in detail herebelow. Stimulator 100 is configured to stimulate tissue, such as to stimulate at least a portion of patient P's brain B, such as via pathway 40. Controller 200 is configured to initiate and/or adjust (hereinafter "set" or "setting") one or more stimulation parameters of stimulator 100, such as one or more test stimulation parameters 106 and/or one or more treatment stimulation parameters 107 (collectively or singly referred to as "stimulation parameters" 105), also as described in detail herebelow. Diagnostic tool 300 is constructed and arranged to measure one or more patient parameters, and to produce diagnostic data 305 representing the measured patient parameters. The measuring of diagnostic data 305 by diagnostic tool 300 can include but is not limited to performing a data measurement function selected from the group consisting of: recording; gathering; assessing; collecting; determining; processing; combining; and combinations of these.

In some embodiments, system 10 is constructed and arranged to treat a neurological disease and/or disorder selected from the group consisting of: probable Alzheimer's Disease; a genetic form of Alzheimer's Disease; Mild Cognitive Impairment; hippocampal damage such as hippocampal damage due to Alzheimer's Disease, anoxia, epilepsy or depression; dementia; amnesia; a memory disorder such as a spatial memory disorder; cognitive impairment associated with Schizophrenia; Parkinson's Disease related cognitive impairment or dementia; neuronal loss; neuronal damage; chemotherapy induced memory impairment; epilepsy; seizure disorder; and combinations of these. In some embodiments, system 10 is constructed and arranged to treat multiple neurological diseases, multiple neurological disorders and/or at least one neurological disease and at least one neurological disorder.

System 10 can be constructed and arranged such that stimulator 100 delivers test stimulation energy to brain B based on one or more test stimulation parameters 106. System 10 can be further constructed and arranged to deliver treatment stimulation energy to brain B based on one or more treatment stimulation parameters 107, such as when the treatment stimulation parameters 107 are based on the diagnostic data 305 produced by diagnostic tool 300. In some embodiments, stimulator 100 is constructed and arranged as is described in reference to stimulator 100 of FIG. 4 described herebelow. In some embodiments, system 10 is used as is described in reference to the method of FIG. 2 herebelow.

Pathway 40 can comprise a wired or wireless pathway as described in detail herein. Stimulator 100 can comprise an implantable stimulator, an external (e.g. non-implanted) stimulator, or it can comprise both implantable and external portions. Controller 200 is configured to communicate with stimulator 100, via pathway 20, such as to set one or more stimulation parameters 105 of stimulator 100. Pathway 20 can comprise a wired or wireless pathway as described herein. Stimulator 100 can comprise a user interface 101, such as a user interface 101 positioned on an external portion of stimulator 100. In some embodiments, system 10 is constructed and arranged such that communication (e.g. wired or wireless communication) can occur between controller 200 and diagnostic tool 300, such as to transfer diagnostic data 305 and/or one or more stimulation parameters 105.

One or more components of system 10 can include another component of system 10, such as when one or more of at least a portion of stimulator 100, controller 200 and diagnostic tool 300 are combined (e.g. within a common housing). For example, at least a portion of stimulator 100 can comprise at least a portion of controller 200, such as when stimulator 100 includes an external portion comprising user interface 101 which is configured to set one or more stimulation parameters 105. In some embodiments, at least a portion of stimulator 100 can comprise at least a portion of diagnostic tool 300, such as when stimulator 100 comprises one or more sensors 430 constructed and arranged to record one or more patient parameters, such as are described in detail herebelow. In some embodiments, one or more sensors 430 are further constructed and arranged to stimulate tissue such as brain tissue. In some embodiments, at least a portion of controller 200 comprises at least a portion of diagnostic tool 300, such as when controller 200 comprises one or more sensors 230 (also as described in detail herebelow) constructed and arranged such that controller 200 can function as a heart rate monitor, a blood pressure monitor and/or other diagnostic tool configured to produce diagnostic data 305.

Diagnostic tool 300 is constructed and arranged to record, gather, assess, collect, determine and/or otherwise measure one or more patient parameters and produce diagnostic data 305 representing these one or more patient parameters. Diagnostic tool 300 can be further constructed and arranged to process (e.g. mathematically process) and/or combine measured data, such as when diagnostic tool 300 comprises one or more algorithms configured to analyze diagnostic data 305, such as one or more algorithms that compare diagnostic data 305 to one or more "stimulation thresholds" (as described herebelow) and record one or more stimulation parameters associated with the one or more stimulation thresholds. In some embodiments, an algorithm is constructed and arranged to determine a stimulation threshold correlating to an undesired clinical event or other undesired patient event (hereinafter "adverse event") as described herein. In some embodiments, an algorithm is constructed and arranged to determine a stimulation threshold correlating to a desired clinical event or other desired patent event (hereinafter "desired event"), such as an event in which a desired memory recall occurs, a desired memory learning is achieved and/or other desired event takes place, as described herebelow.

System 10 (e.g. automatically or semi-automatically) and/or an operator of system 10 can use the diagnostic data 305 to set and/or modify the stimulation provided by stimulator 100. Setting of one or more treatment stimulation parameters 107 using or otherwise based on diagnostic data 305 can be performed to improve therapy achieved by system 10, as described in detail herebelow. Alternatively or additionally, setting of one or more treatment stimulation parameters 107 using or otherwise based on diagnostic data 305 can be performed to at least one of reduce and/or prevent (hereinafter "reduce") an adverse event for patient P, also as is described in detail herebelow. Diagnostic data 305 can be used to determine if an adverse event has occurred or is about to occur. Alternatively or additionally, diagnostic data 305 can be used to determine if a desired event has occurred or is about to occur. In each of these instances, the test stimulation parameters 106 causing the adverse event or desired event represent a stimulation threshold for that particular event.

In some embodiments, a treatment stimulation parameter 107 is set at a level below or otherwise away from (hereinafter "below") the stimulation threshold that caused an adverse event (e.g. as determined in a diagnostic test of the present inventive concepts). In these embodiments, the term "below" does not necessarily correlate to a lower magnitude of stimulation energy, but represents a lower, greater or different value that tends toward avoiding occurrence of the adverse event. For example, if flow rates of 5 ml/hr or less of an agent infused by an external stimulation element 150a (e.g. via a catheter) or an implanted stimulation element 150b, each described herebelow, caused an adverse event, treatment stimulation parameter 107 could be set to a level of more than 5 ml/hr to avoid the adverse event. In some embodiments, a treatment stimulation parameter 107 is set at a safety margin below the stimulation threshold (e.g. a voltage or current level that is less than the level causing the adverse event). In some embodiments, an approximate 50% safety margin is used (e.g. a voltage or current is set to approximately half the voltage or current causing the adverse event). In other embodiments, a safety margin of at least 10% is used, such as a safety margin of at least 20%, 30%, 40% or 50%.

In some embodiments, a treatment stimulation parameter 107 is set at a level at or above (hereinafter "above") a stimulation threshold that caused a desired event (e.g. as determined in a diagnostic test of the present inventive concepts). In these embodiments, the term "above" does not necessarily correlate to a higher magnitude of stimulation energy, but represents a higher, lower or similar value that tends toward causing occurrence of the desired event.

Stimulator 100 can comprise stimulation element 150a, which is configured to generate and/or deliver energy to stimulate brain B or other tissue of patient P. In some embodiments, stimulator 100 further comprises stimulation element 150b, which can also be configured to generate and/or deliver energy to stimulate brain B or other tissue of the patient. Stimulation elements 150a and/or 150b, collectively or singly referred to as "stimulation element 150", can comprise a stimulation delivery element configured to deliver stimulation energy and/or to otherwise stimulate one or more portions of brain B or other tissue of patient P. Alternatively or additionally, stimulation element 150 can comprise a stimulation energy generating element configured to produce energy to stimulate tissue. In some embodiments, stimulation element 150a comprises a stimulation generating element that delivers energy to stimulation element 150b configured as a stimulation delivery element, such as when stimulation element 150b comprises one or more electrodes which receive electrical energy from stimulation element 150a.

In some embodiments, a stimulation element 150 comprises one or more stimulation delivery elements selected from the group consisting of: electrode such as one or more electrodes configured to deliver electrical stimulation energy; magnetic field delivery element; light delivery element such as a visible, ultraviolet or infrared light delivery element; optogenetic delivery element; sound delivery element such as a subsonic wave or ultrasound wave delivery element; agent delivery element such as a chemical or pharmaceutical agent delivery element; and combinations of these. Alternatively or additionally, stimulation element 150 can comprise one or more stimulation generating elements constructed and arranged to deliver a form of energy selected from the group consisting of: electromagnetic energy such as electrical energy and/or magnetic energy; light energy such as visible, ultraviolet and/or infrared light energy; sound energy such as subsonic, sonic or ultrasound energy; and combinations of these. Alternatively or additionally, stimulation element 150 can comprise an agent delivery pump or reservoir; such as a pump configured to deliver a chemical or pharmaceutical agent through one or more catheters or other fluid delivery conduits.

Stimulator 100 can comprise one or more implanted components (e.g. one or more discrete or otherwise physically separated components), one or more components external to the patient P's body, or both at least one implanted component and at least one external component. Stimulator 100 can comprise two or more components, such as two or more components connected with a physical cable including electrically conductive wires and/or optical fibers, or two or more components which transmit and/or receive information via wireless transmission. In some embodiments, stimulator 100 and/or its implanted housing 110 (described herebelow) are configured as is described in applicant's co-pending U.S. patent application Ser. No. 13/655,652, entitled "Deep Brain Stimulation of Memory Circuits in Alzheimer's Disease", filed Oct. 19, 2012, the contents of which is incorporated herein by reference in its entirety.

Stimulator 100 can comprise at least one housing, such as housing 110. Housing 110 can surround electronic components, a power supply such as a battery, stimulation element 150a, and other components such as those described in reference to FIG. 4 herebelow. Housing 110 can be constructed and arranged for implantation in the patient or remain external.

In some embodiments, stimulator 100 comprises at least an implanted portion and stimulation element 150a (positioned within the implanted portion) comprises a signal generator, such as a signal generator constructed and arranged to deliver electrical and/or one or more other forms of energy to stimulation element 150b. In these embodiments, energy generated by stimulation element 150a can travel through a wired or wireless pathway 40 (e.g. a pathway that comprises one or more wires or other energy carrying conduits which pass under the skin from the chest to the brain) to deliver stimulating energy to one or more stimulation elements 150b. Stimulation elements 150b can be positioned on, in and/or proximate patient P's brain B and/or other tissue to be stimulated. In some embodiments, one or more stimulation elements 150b can be positioned in a location selected from the group consisting of: a subdural location; a supradural location; on and/or in the skull; on and/or in the scalp; and combinations of these.

In some embodiments, stimulator 100 comprises at least an external portion and stimulation element 150a is positioned in an external portion of stimulator 100. In these embodiments, an externally positioned stimulation element 150a can be configured to non-invasively deliver energy to tissue. For example, stimulation element 150a can comprise an electromagnetic field generator, a sound generator, a light energy generator, or other energy generator configured to deliver energy non-invasively through the skin through a wireless pathway 40 (e.g. through the skin and skull of patient P) to stimulate one or more portions of brain B. Wireless stimulation transmissions can comprise a transmission selected from the group consisting of: electromagnetic waves; sound waves such as ultrasonic and subsonic waves; light waves; and combinations of these. Non-limiting examples of non-invasive stimulation devices include: one or more transcranial magnetic stimulation devices, such as is described in U.S. Pat. No. 7,087,008, entitled "Apparatus and Methods for Delivery of Transcranial Magnetic Stimulation", filed May 3, 2002, the contents of which is incorporated herein by reference in its entirety; one or more external focused energy delivery devices, such as is described in U.S. patent application Ser. No. 13/169,288, entitled "Systems and Methods for Stimulating Tissue Using Focused Energy", filed Jun. 27, 2011, the contents of which is incorporated herein by reference in its entirety; ultrasound stimulation devices; optogenetics-based stimulation devices; light-based stimulation devices; fiber optic based stimulation devices; and combinations of these.

Pathway 40 can comprise one or more physical conduits such as wires, fluid delivery tubes, and/or optical fibers that connect to one or more electrodes, agent delivery elements and/or other stimulation delivery elements 150b positioned in and/or proximate to a location within brain B or other tissue to be stimulated. Pathway 40 can include a first lead that is positioned to stimulate a specific site in brain B. In these embodiments, stimulation elements 150b can comprise one or more electrodes positioned in the hypothalamic area in proximity to the fornix, and/or at a different location as described herebelow. Stimulator 100 can take the form of a fully implanted signal generator, such as a signal generator similar to signal generator Model 7424, manufactured by Medtronic, Inc. under the trademark Itrel II. Pathway 40 can comprise one or more forms, such as any of the leads compatible with the Model 7424 such as Model 3387 lead set, for stimulating brain B. The lead can be coupled to stimulator 100 by a compatible lead extension.

Controller 200 can be configured to initiate, adjust and/or otherwise set at least one test stimulation parameter 106 and/or treatment stimulation parameter 107, such as a stimulation parameter selected from the group consisting of: voltage level such as an average voltage level, rms voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; agent delivery rate; physiologic concentration; power of light delivered to tissue; frequency of light delivered to tissue; a modulation parameter of light delivered to tissue; amplitude of sound delivered to tissue; frequency of sound delivered to tissue; a modulation parameter of sound delivered to tissue; mass of agent delivered to tissue; volume of agent delivered to tissue; concentration of agent delivered to tissue; delivery rate of agent delivered to tissue; and combinations of these. System 10 test stimulation parameters 106 and/or treatment stimulation parameters 107 can be set by signals sent from controller 200 to stimulator 100 via pathway 20.

In some embodiments, stimulation element 150b comprises up to four implanted stimulation electrodes, such as four electrodes implanted into a portion of brain B using conventional stereotactic surgical techniques. In some embodiments, stimulation element 150b comprises two or more electrodes spaced approximately 1.5 mm apart. Each of the up to four electrodes (stimulation elements 150b) can be individually connected to stimulator 100 through pathway 40 including a first lead with at least one conductor. The first lead can be surgically implanted through a hole in the skull and the at least one conductor can be implanted between the skull and the scalp. The lead with the one or more conductors can be electrically attached to stimulator 100. In some embodiments, at least a portion of stimulator 100 is implanted in a human body, for example in the chest, within an arm, and/or in the abdomen of a human body. In some embodiments, at least a portion of stimulator 100 is implanted in the chest and pathway 40 comprises one or more conductors that are implanted subcutaneously along the head, neck and shoulder to connect a housing of the portion of stimulator 100 implanted in the chest. Pathway 40 can comprise twin leads, a first lead and a second lead (e.g. each including one or more conductors), that are connected to a first electrode (e.g. one or more electrodes) and a second electrode (e.g. one or more electrodes), respectively, the two leads implanted into brain B bilaterally (e.g. bilaterally about the fornix of brain B), with each lead connected to a single stimulator 100 portion. Alternatively, the second lead and second electrode can be supplied with stimulating pulses from a separate stimulator 100 portion (e.g. a second portion implanted in the chest or other internal location of the patient P). In some embodiments, first and second leads are also attached (e.g. on the opposite end) to a stimulation element 150b comprising two or more electrodes, such as two electrodes positioned in two separate nuclei that potentiate each other's effects. In some embodiments, the first and second leads are attached to a stimulation element 150b comprising two electrodes in two separate nuclei with opposite effects, with the dual stimulation delivered being used to fine-tune the response through opposing forces. It will be appreciated, however, that any number of electrodes or other stimulation elements 150a and/or 150b can be positioned within brain B, on or proximate to brain B, remote from brain B, and/or external to the patient P's body, in accordance with the present inventive concepts. Additionally, one or more secondary electrodes or secondary stimulation elements can be implanted or otherwise positioned so that a secondary stimulation portion lies in communication with another predetermined portion of a brain.

System 10 can be utilized in monopolar and/or multipolar electrical stimulation configurations (e.g. monopolar, bipolar and/or stimulation configurations including 3 or more poles). In some embodiments, system 10 delivers monopolar energy, such as when housing 110 and at least a portion of stimulator 100 are implanted in the patient, such that housing 110 can function as a lead (e.g. a positive lead). In these embodiments, stimulation element 150b can comprise one or more electrodes positioned in brain B, the one or more electrodes functioning as the associated lead (e.g. as negative leads).

System 10 can be constructed and arranged to provide stimulation continuously and/or intermittently, such as for a chronic period of time of at least 1 month, at least 3 months or at least 6 months. In some cases, stimulation can be provided for a longer period of time such as 12 months or more. Intermittent stimulation can include delivery of constant or pulsed stimulation energy with stimulation "on" times of at least 30 minutes, or at least 60 minutes. In some embodiments, the constant or pulsed stimulation energy delivery duty cycle (ratio of "on" time to the sum of "on" time plus "off" time) ranges from 20% to 80%. Stimulation can be performed in either an open loop mode or a closed loop mode. In some embodiments, stimulation is initiated and/or modified to achieve an acute goal (e.g. by a caregiver or the patient), such as to perform an acute task or activity in which enhanced memory function is desirable. Stimulation can comprise delivery of electrical energy, sound energy, chemical energy, light energy, and/or the delivery of a pharmaceutical drug or other agent. Stimulation elements 150a and/or 150b configured as electrodes can be of various forms selected from the group consisting of: single component bipolar electrode; multiple unipolar electrodes; stacked contact electrodes; discrete electrodes; electrode strip; grid of electrodes; paddle electrode; high-density/high channel or lead count micro-electrodes; and combinations of these.

Stimulator 100 can include an agent delivery mechanism, such as a mechanism including a pump and one or more catheters configured to deliver one or more agents to one or more brain or other body locations. In some embodiments, system 10 is constructed and arranged to deliver both electrical stimulation and agent delivery, sequentially and/or simultaneously. In these embodiments, a pump can be implanted below the skin of patient P, such as when the pump has an access port into which a needle can be inserted through the skin to inject a quantity of a liquid agent, such as a medication or other drug. The liquid agent is delivered from the pump through a catheter (e.g. after traveling from a pumping chamber and through a catheter access port attached to the side of the pump), and into patient P. The catheter can be positioned to deliver the agent to one or more specific infusion sites of brain B. The pump can take the form of any number of known implantable pumps including for example that which is disclosed in U.S. Pat. No. 4,692,147, "Drug Administration Device", the contents of which is incorporated herein by reference in its entirety. The distal end of the catheter can terminate in a cylindrical hollow tube having a distal end implanted, such as by conventional stereotactic surgical techniques, into a portion of brain B to affect tissue within brain B. The tube can be surgically implanted through a hole in the skull and the catheter can be implanted between the skull and the scalp, with the catheter fluidly attached to the pump. The pump can be implanted in a subcutaneous pocket located in the chest below the clavicle. Alternatively, the pump can be implanted in the abdomen. The catheter can include twin tubes (e.g. two separate catheters attached to a single pump or a single catheter with two lumens) that have their distal portions implanted into brain B in bilateral locations. Alternatively, a second catheter can be implanted, for example on the other side of brain B, and can be supplied with drugs or other stimulating agents from a separate pump. The one or more pumps can be programmed to deliver one or more agents according to a particular dosage and/or time interval. For example, a pump can deliver drug therapy over a first period with a high dose configured to induce a high level of neurogenesis, after which a lower dose is delivered to maintain neurogenesis and secondary trophic effects (e.g. axonal sprouting and synaptogenesis). Any number of neurotrophins or drugs that stimulate neurons can be administered including, but not limited to: NGF; BDNF; NT-3; FGF; EGF; GDNF; Neurteurin; Artemin; Persephin; and combinations of these.

System 10 can be constructed and arranged to modulate memory circuits to produce clinical benefits, such as to modulate memory circuits in the brain B of patient P to reduce the progression of or otherwise treat the effects of Alzheimer's Disease (AD). System 10 can modulate memory circuits in brain B via electrical or other stimulation means. System 10 can be constructed and arranged to stimulate brain B tissue selected from the group consisting of: fornix; entorhinal cortex; hippocampus; anterior thalamic nucleus; amygdala; mammillary bodies; parahippocampal cortex; temporal neocortex; septal nuclei; nucleus basalis of Meynert; subcallosal or subgenual cingulate; ventral capsule; ventral striatum; and combinations thereof. In some embodiments, the brain tissue stimulated comprises brain tissue selected from the group consisting of: Papez Circuit; hippocampus; cingulate gyrus; fornix; a mammilothalamic tract; amygdala; hypothalamus; mammillary bodies; septal nuclei; temporal neocortex; the medial forebrain bundle; anterior and mediodorsal nuclei of the thalamus; the diagonal band of the Broca; temporal stem and temporal white matter; brainstem; nucleus basalis of Meynert; anterior thalamic nucleus; entorhinal cortex; rhinal cortex; periventricular zone; anterior thalamus; anterior insula; caudate; dorsal anterior cortex; dorsal cingulate; medial frontal cortex; nucleus accumbens; orbital frontal cortex; parietal region; periaqueductal gray area; posterior cingulate area; subcallosal area; subcallosal cingulate; subgenual cingulate; Brodmann area 10; Brodmann area 24; Brodmann area 25; Brodmann area 11/Brodmann area 10; Brodmann area 24b; Brodmann area 31; Brodmann area 32/Brodmann area 10; Brodmann area 32/Brodmann area 11; Brodmann area 39; Brodmann area 46; Brodmann area 46/Brodmann area 9; Brodmann area 47; Brodmann area 6; Brodmann area 9; ventral/medial prefrontal cortex area; ventral/medial white matter; dorsolateral prefrontal cortex; premotor cortex; ventrolateral prefrontal cortex; dorsal anterior cingulate caudate nucleus; frontal pole periaqueductal gray area; dorsolateral prefrontal area; subsingular cingulate; parahippocampal cortex; parahippocampal gyrus; ventral capsule; ventral striatum; and combinations thereof. In some embodiments, the brain tissue stimulated does not comprise tissue selected from the group consisting of: hippocampal tissue; optical tract tissue; and combinations thereof. In some embodiments, the brain tissue stimulated does not comprise tissue selected from the group consisting of: posterior hypothalamic area; ventral tegmental area; lateral hypothalamic area; anterior hypothalamic nucleus; paraventricular nucleus; dorsal medial hypothalamic nucleus; ventromedial hypothalamic nucleus; arcuate nucleus; lateral tuberal nucleus; medial preoptic nucleus; supraoptic nucleus; and combinations thereof. The stimulation site within one or more locations of brain B tissue can be used to stimulate, activate or otherwise affect one or more similar or different brain B tissue locations, such as a stimulation configured to affect a brain B location selected from the group consisting of: fornix; hippocampus; parahippocampal gyrus; entorhinal cortex; amygdale; mammillary bodies; parahippocampal cortex; temporal neocortex; septal nuclei; nucleus basalis of Meynert; subcallosal or subgenual cingulate; and combinations of these. Alternatively or additionally, system 10 and one or more stimulation elements 150 can be constructed and arranged to stimulate non-brain tissue, such as nerve or organ tissue separate from the brain. Stimulated tissue can comprise tissue selected from the group consisting of: vagus nerve; trigeminal nerve; carotid sinus; spinal cord; dorsal root ganglia; tibial nerve; sacral nerve; gastric nerve; and combinations thereof. In some embodiments, system 10 is constructed and arranged to stimulate at least a portion of the hypothalamus, such as at least a portion of the fornix. The fornix is a large axonal bundle that constitutes a major inflow and output pathway from the hippocampus and medial temporal lobe. The hippocampus is a critical component of the limbic circuitry and is distinguished among some of the regions of the brain by persistent production of new neurons. The fornix is involved in memory formation and is known to be affected early in the progression of AD.

In some embodiments, loss of fornix integrity associated with hippocampal volume loss can be detected by diagnostic tool 300 and used by system 10 to predict the progression of AD.

System 10 can be constructed and arranged to sustain and/or improve the function of the fornix. Alternatively or additionally, system 10 can be constructed and arranged to therapeutically affect the hippocampus and/or cortical circuits (e.g. the cortico-cortico circuits). Stimulation of the fornix by system 10 can be used to activate the hippocampus and cortical regions in brain B's default network, a network of brain regions that are active when the individual is not focused on the outside world and/or the brain is at wakeful rest. Patients with AD can exhibit a decrease in glucose metabolism over time. System 10 can be constructed and arranged to increase or maintain (e.g. prevent the decrease of) glucose metabolism, such as by stimulating at least the fornix. System 10 can be constructed and arranged to increase or maintain (e.g. prevent the decrease of) one or more portions of hippocampal volume, such as by stimulating the fornix or other brain B location as described hereabove. In some embodiments, the stimulation of system 10 results in neurogenesis, such as hippocampal neurogenesis.

System 10 can be constructed and arranged to produce clinical benefits to patient P by modulating neurophysiologic activity in pathological circuits. The pathological circuits can be causing functional impairment in the neural elements and circuits underlying cognitive and/or memory functions, and the stimulation provided by system 10 can improve clinical and/or neurobiological outcomes that result from these pathological circuits. Stimulation provided by system 10 can be used to modulate dysfunctional networks, such as to therapeutically manipulate the levels of one or more deleterious proteins.

System 10 can be constructed and arranged to drive activity in projection structures downstream from the stimulation site (e.g. downstream from the fornix). System 10 can be constructed and arranged to provide evoked responses that are unequivocal and/or consistent. Stimulation received by system 10 can activate the cingulated gyrus and precuneus area of the parietal lobe, including direct and trans-synaptic sequential activation of downstream targets related to the connectivity of the fornix and hippocampus.

System 10 can be constructed and arranged to regulate the level of one or more neurotrophic factors and/or neurotransmitters. System 10 can be constructed and arranged to ameliorate cognitive decline associated with dementia. A patient receiving therapy from system 10 can have reduced integrity of white matter tracts innervating limbic structures such as the fornix (e.g. at least the fornix) as determined by fractional anisotropy maps using diffusion tensor imaging. System 10 can be constructed and arranged to achieve at least one of: treats memory impairment; improves memory function; treats cognitive function loss; reverses synaptic loss; improves cognitive function; reduces degradation of cognitive function; promotes neurogenesis in the hippocampus of patient P's brain B; drives neurotrophin expression; regulates one or more biomarkers related to Alzheimer's Disease such as amyloid-beta, tau, and/or phosphorylated tau; regulates BDNF expression; increases neurotransmitter release such as acetylcholine; or improves glucose utilization in the temporal lobe, the parietal lobe or both lobes of the patient's brain.

In some embodiments, a combination of treatment therapies can be delivered by system 10 to provide influencing of multiple neuronal types. Stimulator 100 can be constructed and arranged to deliver multiple therapies, such as two or more stimulation therapies selected from the group consisting of: electrical stimulation; magnetic stimulation; optical stimulation (e.g. visible, ultraviolet and/or infrared light); sound stimulation (e.g. ultrasound or subsonic waves); chemical stimulation (e.g. a drug or other agent); and combinations of these, such as described hereabove. For example, it can be desirable to concurrently influence, via chemical, electrical and/or other stimulation, the neurons in the fornix, hippocampus and/or other portions of brain B to achieve an improved result. Such a system 10 utilizing multiple forms of treatment therapy can be similar to that which is disclosed, for example, in U.S. Pat. No. 5,782,798, the content of which is incorporated herein by reference in its entirety. In addition to affecting the deep brain, it can be desirable for system 10 to concurrently affect one or more other portions of the brain.

In some embodiments, system 10 is constructed and arranged to provide one or more pharmaceutical or other agents, such as an agent delivered orally, via an injection, or delivered by a component of system 10. In some embodiments, system 10 is constructed and arranged to provide a cholinesterase inhibitor medication or other agent to patient P. Stimulation element 150a and/or 150b can be constructed and arranged to deliver one or more pharmaceutical or other agents, such as when stimulation 150a and/or 150b are further configured as a drug delivery element or other liquid or solid dispensing element.

As described above, controller 200 is constructed and arranged to set one or more treatment stimulation parameters 107 of system 10, such as an initial setting of one or more treatment stimulation parameters 107 (e.g. to cause an initial treatment stimulation energy to be delivered to brain B) or a modification to an existing set of one or more treatment stimulation parameters 107 (e.g. to modify the treatment stimulation energy being delivered to brain B). Initial settings of treatment stimulation parameters 107 and/or modifications to existing settings can be made to provide sufficient therapy (e.g. cause a desired event) and/or to reduce the likelihood or effect of one or more adverse events. Setting of one or more treatment stimulation parameters 107 can be made by an operator of system 10 using controller 200, such as an operator who is a clinician or other caregiver to patient P. Alternatively or additionally, setting of one or more treatment stimulation parameters 107 can be performed automatically or semi-automatically by system 10, such as in a closed loop fashion based on information received from diagnostic tool 300 or another component of system 10.

Controller 200 comprises user interface 201, such as a user interface configured to provide information to and/or receive commands from an operator of system 10. User interface 201 can comprise one or more user input and/or user output components selected from the group consisting of: a touchscreen; a graphical and/or alphanumeric screen; a keypad; a mouse; and combinations of these. Controller 200 can comprise one or more discrete controllers, such as one or more handheld devices configured to program or otherwise communicate with stimulator 100 and/or diagnostic tool 300. Pathway 20 can comprise a uni-directional or bi-directional communication pathway between controller 200 and stimulator 100. Pathway 20 can comprise one or more physical conduits such as electrically conductive wires and/or optical fibers. Alternatively or additionally, pathway 20 can comprise a wireless communication pathway, such as a transmission of electromagnetic waves such as is used in wireless radiofrequency (RF) communications.

Diagnostic tool 300 can comprise a user interface 301, such as a user interface configured to provide information to and receive commands from an operator of system 10. User interface 301 can comprise one or more user input and/or user output components selected from the group consisting of: a touchscreen; a graphical and/or alphanumeric screen; a keypad; a mouse; and combinations thereof. As described above, diagnostic tool 300 is constructed and arranged to measure one or more patient parameters and produce diagnostic data 305 which is determined based on the one or more measured patient parameters. Diagnostic data 305 can be displayed on user interface 301 (such as heart rate information, blood pressure information, or other data corresponding to a measured patient parameter that is displayed on user interface 301). In some embodiments, diagnostic tool 300 can communicate directly with controller 200 and/or stimulator 100, such as via a wired or wireless connection as described herein, such that diagnostic data 305 is recorded by controller 200 and/or stimulator 100, such as to automatically and/or semi-automatically modify one or more stimulation parameters 105.

As described herein, diagnostic data 305 can be used to determine if an adverse event has occurred or is about to occur. Treatment stimulation parameters 107 can be set at a level below or otherwise different than the stimulation threshold at which the adverse event occurred, such as at a safety margin below or otherwise away from that stimulation threshold (e.g. a voltage or current level that is less than the level causing the adverse event). In some embodiments, one or more treatment stimulation parameters 107 are modified based on a stimulation threshold (e.g. modified to a level at or below the stimulation threshold, such as at a safety margin below the stimulation threshold at which an adverse event occurred). For example, an adverse event that occurs at a signal voltage of 6 Volts, may result in delivering therapy at 5 Volts (a 16.6% safety margin), at 4 Volts (a 33.3% safety margin) or at 3 Volts (a 50% safety margin).

Diagnostic tool 300 can comprise one or more diagnostic devices, such as one or more devices selected from the group consisting of: heart rate monitor; EKG measurement device; oximeter; combined heart rate and oximeter device such as a pulse oximeter; blood pressure measurement device; neuronal activity measurement device; EEG measurement device; evoked response potential (ERP) measurement device; neurochemical analysis device; memory test device; memory test form; respiration measurement device; sweat measurement device; skin conductivity measurement device; pH measurement device; body motion measurement device; imaging device; and combinations of these. Diagnostic tool 300 can be constructed and arranged to detect and/or record an adverse event, such as an adverse event selected from the group consisting of: undesirable heart rate; undesirable respiration rate; undesirable sweating; undesirable hallucinations; undesirable tingling; flushing; undesirable psychiatric effect; undesirable cognitive effect; unpleasant generalized warming; undesirable perceptions described as déjà vu; seizure; synchronized neuronal firing pattern; undesired neural response time; undesired brain state; undesired theta phase; undesired p300 amplitude; and combinations of these.

In some embodiments, diagnostic tool 300 comprises two independent diagnostic measurement devices, for example two devices whose diagnostic data are used in combination. For example, diagnostic tool 300 can comprise a blood pressure measurement device and a heart rate measurement device, such as to identify patient discomfort or other patient issue (e.g. a falsehood or other inaccurate statement made by the patient that can be detected through analysis of a patient parameter such as heart rate and/or blood pressure).

Diagnostic tool 300 can comprise a memory test such as a verbal, visual, motor function and/or spatial memory test. Diagnostic tool 300 can be constructed and arranged to detect and/or record a memory recall event, such as a tool including an EEG measurement device and/or a form (e.g. a paper form or electronic form) configured to manually record the results of a memory test.

In embodiments where diagnostic tool 300 comprises an EKG measurement device, one or more treatment stimulation parameters 107 can be set based on a stimulation threshold at which undesired EKG activity (e.g. tachycardia or an arrhythmia) is identified in diagnostic data 305.

In embodiments where diagnostic tool 300 comprises a neuronal activity measurement device, diagnostic tool 300 can be constructed and arranged to measure a neuronal parameter selected from the group consisting of: single neuron activity; local field potential (LFP); event related potential (ERP); electroencephalogram reading; electrocorticogram reading; and combinations of these. In these embodiments, a stimulation threshold (e.g. a stimulation threshold at which an adverse event is recorded by diagnostic tool 300) can be determined when an adverse event occurs that is selected from the group consisting of: seizure; synchronized neuronal firing pattern; undesired neural response time; undesired brain state; undesired theta phase; undesired p300 amplitude; and combinations of these.

In embodiments where diagnostic tool 300 comprises an event related potential (ERP) measurement device, one or more treatment stimulation parameters 107 can be set based on a stimulation threshold at which undesired ERP activity is identified in diagnostic data 305.

In embodiments where diagnostic tool 300 comprises a blood pressure measurement device, one or more treatment stimulation parameters 107 can be set based on a stimulation threshold at which undesired blood pressure readings (e.g. above a threshold) are identified in diagnostic data 305. In these embodiments, diagnostic tool 300 can further comprise a heart rate measurement device, such that diagnostic data comprises both blood pressure readings and heart rate readings, such as when a stimulation threshold is based on the occurrence of high blood pressure and/or tachycardia.

In embodiments where diagnostic tool 300 comprises a blood oxygen measurement device, one or more treatment stimulation parameters 107 can be set based on a stimulation threshold at which undesired blood oxygen readings are identified in diagnostic data 305.

In embodiments where diagnostic tool 300 comprises a body motion measurement device, one or more treatment stimulation parameters 107 can be set based on a stimulation threshold at which undesired body motion (e.g. a tremor) is identified in diagnostic data 305.

In embodiments where diagnostic tool 300 comprises a neurochemical analysis device, the neurochemical analysis device can be constructed and arranged to measure a parameter selected from the group consisting of: neurotransmitter level (GABA, glutamate, acetylcholine, dopamine, epinephrine, etc.); a pH concentration; an ion concentration; a lactate level; cerebral blood flow; glucose utilization; oxygen extraction; and combinations of these. One or more treatment stimulation parameters 107 can be set based on a stimulation threshold at which undesired neurochemical activity and/or level is identified in diagnostic data 305.

In embodiments where diagnostic tool 300 comprises an imaging device, one or more treatment stimulation parameters 107 can be set based on a stimulation threshold at which an undesired patient condition is identified in one or more images (diagnostic data 305) produced by the imaging device. Diagnostic tool 300 can comprise an imaging device selected from the group consisting of: standardized Low Resolution Brain Electromagnetic Tomography (sLORETA) device; functional magnetic resonance imaging (fMRI); MagnetoEncephalography (MEG); and combinations of these, such as when used to produce diagnostic data 305 that quantifies or qualifies the effects of receiving stimulation from system 10. In these embodiments, one or more images produced by diagnostic tool 300 can be used to optimize therapy or reduce an adverse event, such as when used to select an electrode to receive stimulation energy based on its position relative to a target as described herein. One or more images produced by diagnostic tool 300 can be use to select one or more stimulating elements from a set of multiple stimulating elements (e.g. to select one or more electrodes from a set of multiple electrodes based on an image of the multiple electrodes in reference to a target stimulation location such as the fornix).

In some embodiments, diagnostic tool 300 produces data (e.g. image data) to assess axonal pathways, such as an assessment performed during stimulation of the axonal pathways or locations proximate the assessed pathways. In these embodiments, diagnostic data 305 produced by diagnostic tool 300 can be used to identify one or more axonal pathways that may be necessary or at least desirable to optimize therapeutic benefit from the stimulation provided by system 10. Diagnostic tool 300 can comprise at least a diffusion tension imaging (DTI) device and/or a tractography-activation model (TAM) used to identify the pathways stimulated by system 10. The TAM can consist of: anatomical and diffusion-weighted imaging data acquired on the patient; probabilistic tractography from the brain region surrounding the stimulation element 150a and/or 150b; finite element models of the electric field generated by stimulator 100; and/or application of the electric field produced by stimulation element 150a and/or 150b to multi-compartment cable models of axons, with trajectories defined by the tractography, to predict action potential generation in the pathways. Diagnostic tool 300 can be configured to produce clinical data, diffusion tensor tractography, and/or computer models of tissue-specific stimulation areas, such as to determine one or more axonal pathways being stimulated and/or to predict or differentiate the therapeutic benefit of their stimulation.

Diagnostic tool 300 can comprise a patient assessment recording tool, such as a tool selected from the group consisting of: a form; a paper form; an electronic form; a tablet; a personal computer; a database; and combinations of these. In these embodiments, the patient assessment can comprise an assessment selected from the group consisting of: an assessment received verbally from the patient; an assessment received in written form from the patient; an assessment made by a caregiver of the patient; and combinations of these. The patient assessment can comprise an assessment of a patient state selected from the group consisting of: depression; paranoia; schizophrenia; suicidality; suicide ideation; apathy; anxiety; mania; and combinations of these. Diagnostic tool 300 can comprise an algorithm configured to analyze data on a patient assessment form or other patient assessment tool.

In some embodiments, diagnostic tool 300 comprises one or more sensors 330 as shown. One or more sensors of system 10, such as sensor 330, sensor 230 and/or sensor 430 can comprise a sensing element selected from the group consisting of: neuronal activity sensor; EEG sensor; local field potential (LFP) sensor; neurochemical sensor; pH sensor; pressure sensor; blood pressure sensor; optical sensor; blood gas sensor; blood oxygen sensor; magnetic sensor; strain gauge; and combinations of these. Sensor 330, sensor 230 and/or sensor 430 can comprise an implanted or external sensor. Stimulating element 150a and/or 150b can comprise sensor 330. Sensor 330, sensor 230 and/or sensor 430 can comprise at least one electrode. System 10 can be constructed and arranged to provide closed loop stimulation based on one or more signals received from one or more of sensors 330, 230 and/or 430.

As described hereabove, one or more portions of stimulator 100 can be implanted in the patient, such an implantation of stimulation element 150b. Diagnostic tool 300 can be constructed and arranged to gather diagnostic data 305 before and/or after implantation of stimulation element 150b. In some embodiments, diagnostic tool 300 gathers diagnostic data 305 to determine a stimulation threshold at least 5 minutes after implantation of stimulation element 150b. In some embodiments, diagnostic tool 300 gathers diagnostic data 305 to determine a stimulation threshold at least 24 hours after implantation of stimulation element 150b, or at least 2 weeks after implantation of stimulation element 150b.

As described above, controller 200 and stimulator 100 can be constructed and arranged to stimulate brain B with one or more temporary stimulation parameters, test stimulation parameters 106. Diagnostic tool 300 can be constructed and arranged to measure one or more patient parameters while brain B is being stimulated with test stimulation parameters 106, producing diagnostic data 305 correlating to the test stimulation parameters 106. In some embodiments, multiple sets of similar or dissimilar test stimulation parameters 106 are delivered to brain B, while diagnostic tool 300 measures at least one patient parameter and produces diagnostic data 305. In some embodiments, a series of varied test stimulation parameters 106 can be delivered to brain B (e.g. a stepped or continuous increase in stimulation energy level, such as a stepped or continuous increase of a stimulating voltage and/or current), while diagnostic tool 300 measures one or more patient parameters and produces a set of diagnostic data 305 which is correlated to the particular level of test stimulation parameters 106 associated with each subset of diagnostic data 305. Subsequently, stimulator 100 delivers treatment stimulation energy comprising one or more treatment stimulation parameters 107 that are determined from or otherwise based on the produced diagnostic data 305. In some embodiments, one or more treatment stimulation parameters 107 are manually programmed into stimulator 100 via controller 200. In some embodiments, system 10 is constructed and arranged to automatically set one or more treatment stimulation parameters 107 based on the produced diagnostic data 305.

In some embodiments, diagnostic data 305 produced by diagnostic tool 300 is used to determine an initial (e.g. first time) set of treatment stimulation parameters 107. In some embodiments, diagnostic data 305 produced by diagnostic tool 300 is used to modify a pre-existing set of treatment stimulation parameters 107. In some embodiments, diagnostic data 305 produced by diagnostic tool 300 is used to determine test stimulation parameters 106, such as diagnostic data 305 collected in a previous test. In these embodiments, a test stimulation parameter 106 can be set based on a stimulation threshold at which an adverse event was detected by diagnostic tool 300.

In some embodiments, stimulator 100 stimulates brain B with a first set of test stimulation parameters 106' for a first time period and a second set of test stimulation parameters 106" for a second time period. The first time period and the second time period can comprise relatively the same length of time or different lengths of time. The first and/or second time periods can comprise a time period less than or equal to 24 hours, such as less than or equal to 6 hours, 3 hours, 1 hour, 30 minutes, 15 minutes, 10 minutes, 5 minutes or 2 minutes. Diagnostic tool 300 measures one or more patient parameters during all or a portion of both the first time period and the second time period, and produces first diagnostic data 305' and second diagnostic data 305", representing the measured at least one patient parameter recorded during the first time period and the second time period, respectively. Subsequently, stimulator 100 provides stimulation energy to brain B comprising one or more treatment stimulation parameters 107 that are determined using or otherwise based on the first diagnostic data 305' and second diagnostic data 305". In these embodiments, treatment stimulation parameters 107 can be based on one or more test stimulation parameters 106 associated with a desired treatment and/or they can be based on one or more test stimulation parameters 106 associated with avoiding an adverse event, such as described herein.

In some embodiments, the treatment stimulation parameters 107 equal or at least approximate the first set of test stimulation parameters 106' or the second set of test stimulation parameters 106". The treatment stimulation parameters 107 chosen can approximate a test stimulation parameter 106 associated with an improved or otherwise desired treatment of a neurological disease and/or disorder. The improved treatment can correspond with a therapeutic benefit such as a desired memory recall with the patient. Alternatively or additionally, the treatment stimulation parameters 107 chosen can approximate a test stimulation parameter 106 associated with avoidance of an adverse event. In some embodiments, the treatment stimulation parameters 107 chosen can be proportional or otherwise based on a test stimulation parameter 106 associated with avoidance of an adverse event as described hereabove, such as when treatment stimulation parameters 107 are a safety margin below the test stimulation parameters 106 at which the adverse event occurred, as described herein.

In some embodiments, one or more treatment stimulation parameters 107 are manually programmed into stimulator 100 via controller 200. Alternatively, system 10 is constructed and arranged to automatically set one or more treatment stimulation parameters 107 based on the produced diagnostic data 305.

Diagnostic tool 300 used in the first time period and the second time period can comprise one or more diagnostic devices or other tools, such as are described herein, each producing diagnostic data 305. In some embodiments, diagnostic data 305 produced by a diagnostic tool 300 is used to determine first test stimulation parameters 106' and/or second test stimulation parameters 106", such as diagnostic data 305 collected in a previous test performed using diagnostic tool 300. In some embodiments, diagnostic tool 300 comprises a memory test tool, such as a form used to record memory data. In these embodiments, treatment stimulation parameters 107 can approximate or otherwise be based on the test stimulation parameters 106 that resulted in a higher memory test score recorded in one of a set of time periods (e.g. two or more time periods) between which one or more test stimulation parameters were varied.

One or more treatment stimulation parameters 107 can comprise an electrical stimulation parameter selected from the group consisting of: voltage level such as an average voltage level, rms voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; and combinations of these. In some embodiments, stimulation element 150*b* comprises a lead inserted into brain B and comprising multiple electrodes, and a treatment stimulation parameter 107 or other stimulation parameter 105 can represent a selection (e.g. a subset) of one or more specific electrodes of the lead to receive stimulation energy. The selection of electrodes can comprise a single electrode, a pair of electrodes, or more than two electrodes, such as one or more electrodes that receive monopolar or bipolar energy. In some embodiments, a stimulation parameter 105 comprises a signal voltage of between 0.1 Volts and 10.0 Volts, such as a voltage between 1.0 Volts and 6.0 Volts, or between 1.0 Volts and 3.0 Volts. In some embodiments, a stimulation parameter 105 comprises a voltage less than or equal to 9.0 Volts, such as less than or equal to 8.0 Volts, 7.0 Volts, 6.0 Volts, 5.0 Volts, 4.0 Volts or 3.5 Volts. In some embodiments, a stimulation parameter 105 comprises a signal frequency between 2 Hz and 1000 Hz, such as a frequency of approximately 130 Hz. Energy delivery can be given in a series of on and off times, such as when a stimulation parameter 105 comprises an on-time of approximately 30 μseconds to 200 μseconds, such as with an on time of 90 μseconds. A stimulation parameter 105 can comprise a parameter associated with duration of energy delivery, such as a parameter corresponding to continuous delivery of energy (e.g. continuous delivery of pulsed energy) or a parameter corresponding to intermittent energy delivery comprising one or more energy delivery periods ranging from thirty minutes to 24 hours.

In some embodiments, a stimulation parameter 105 comprises a light stimulation parameter selected from the group consisting of: power of light delivered to tissue; frequency of light delivered to tissue; modulation parameter of light delivered to tissue; and combinations of these.

In some embodiments, a stimulation parameter 105 comprises a sound stimulation parameter selected from the group consisting of: amplitude of sound delivered to tissue; frequency of sound delivered to tissue; modulation parameter of sound delivered to tissue; and combinations of these.

In some embodiments, a stimulation parameter 105 comprises an agent delivery stimulation parameter selected from the group consisting of: mass of agent delivered to tissue; volume of agent delivered to tissue; concentration of agent delivered to tissue; delivery rate of agent delivered to tissue; and combinations of these.

In some embodiments, controller 200 and/or another component of system 10 are constructed and arranged to set at least one treatment stimulation parameter 107 based on a stimulation threshold at which an adverse event is detected by diagnostic tool 300, such as an adverse event as described hereabove. In these embodiments, the at least one treatment stimulation parameter 107 can be set to a level at or below the stimulation threshold, such as at a safety margin below the stimulation threshold as described hereabove.

In some embodiments, controller 200 and/or another component of system 10 are constructed and arranged to set at least one treatment stimulation parameter 107 based on a stimulation threshold at which a desired event is detected by diagnostic tool 300. Patient desired events include events selected from the group consisting of: recall of a desired memory; achievement of desired memory learning; desired level of neuronal activity; acceptable physiologic condition such as an acceptable heart rate or acceptable level of neuronal activity; experiential phenomena such as those described in epilepsy literature; and combinations of these. In these embodiments, the at least one treatment stimulation parameter 107 can be set to a level at or above the stimulation threshold, such as at a pre-determined percentage above the stimulation threshold. In these embodiments, the at least one treatment stimulation parameter 107 can also be set based on a second stimulation threshold at which an adverse event occurred, such as a safety margin below the adverse event stimulation threshold. For example, a memory recall event may be recorded by diagnostic tool 300 at a stimulation voltage of X Volts, and an adverse event may be recorded by diagnostic tool 300 at a stimulation voltage of Y Volts, where Y is greater than X. A treatment stimulation parameter 107 can be set to a signal voltage between X Volts and Y Volts.

System 10 can be constructed and arranged to provide open loop stimulation to brain B. Alternatively or additionally, system 10 can be constructed and arranged to provide closed loop stimulation to brain B, such as closed loop stimulation based on diagnostic data 305 provided by diagnostic tool 300 and/or a signal provided by one or more of sensors 330, 430 and 230, or a separate implanted or external sensor, such as sensor 430 described in reference to FIG. 4 herebelow.

In some embodiments, diagnostic tool 300 and/or another component of system 10 comprises data logging assembly 350. Data logging assembly 350 can be constructed and arranged to record one or more events that occur during delivery of test stimulation energy using test stimulation parameters 106, such as when stimulation energy is varied. Data logging assembly 350 can be configured to record diagnostic data 305, such as to determine a minimum, maximum, average and/or other statistical value of diagnostic data 305 (e.g. a maximum heart rate and/or a maximum blood pressure that occurs during delivery of test stimulation energy). In some embodiments, data logging assembly 350 comprises an assembly with a button that a patient can activate (e.g. press), such as during a patient adverse event or a memory recall event, as noticed by the patient. In some embodiments, at least a portion of data logging assembly 350 can be at a location remote from the patient, such as at one or more file locations accessible via the Internet or other information access network. Diagnostic data 305 from multiple patients could be stored in one or more locations remote from those patients. Diagnostic data 305 recorded by one or more diagnostic tools 300 during diagnostic tests performed on one or more patients can be processed, analyzed and/or otherwise used to determine one or more treatment stimulation parameters 107 for one or more patients.

Figure 2:
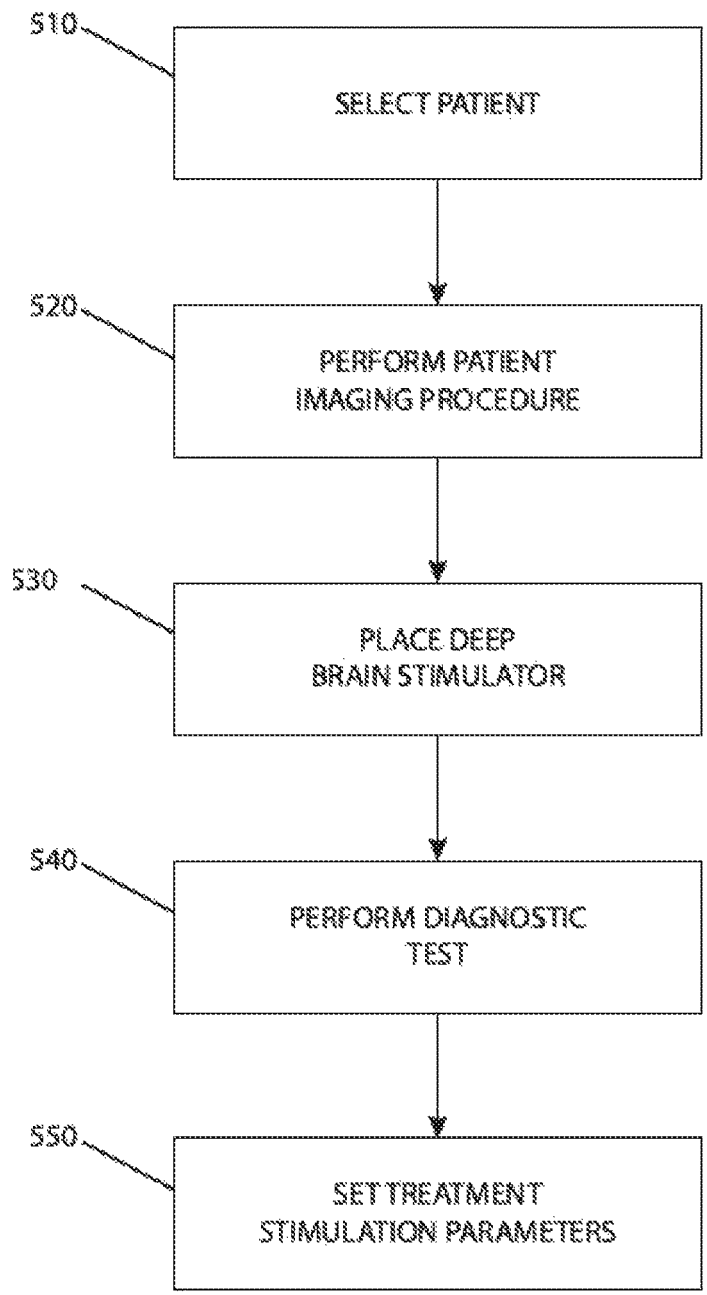
FIG. 2 illustrates a flow chart of a method for treating a patient with a brain stimulation system, consistent with the present inventive concepts.

Referring now to FIG. 2 a flow chart of a series of steps for treating a patient with a stimulation system is illustrated, consistent with the present inventive concepts. The method comprises STEPs 510 through 550, which can be performed using one or more components of system 10 of FIG. 1 described hereabove. In STEP 510, a patient is selected for implantation. In a preferred method, the patient is screened for candidacy as described in reference applicants co-pending U.S. patent application Ser. No. 13/655,652, entitled "Deep Brain Stimulation of Memory Circuits in Alzheimer's Disease", filed Oct. 19, 2012, the content of which is incorporated herein by reference in its entirety. In some embodiments, the selected patient is a patient diagnosed and/or prognosed with a cognitive disorder selected from the group consisting of: Alzheimer's Disease (AD) such as Mild or Moderate Alzheimer's Disease; probable Alzheimer's Disease; a genetic form of Alzheimer's Disease; Mild Cognitive Impairment (MCI); hippocampal damage such as hippocampal damage due to Alzheimer's disease, anoxia, epilepsy or depression; neuronal loss; neuronal damage; chemotherapy induced memory impairment; epilepsy; a seizure disorder; dementia; amnesia; a memory disorder such a spatial memory disorder; cognitive impairment associated with Schizophrenia; Parkinson's Disease related cognitive impairment or dementia; and combinations of these. Additionally or alternatively, the patient can be selected to treat negative symptoms of a disease or disorder selected from the group consisting of: schizophrenia; depression; other conditions of reversible impaired memory or cognition; and combinations of these.

In STEP 520, at least one imaging procedure is performed on the patient, collecting at least one patient image. In some embodiments, the imaging procedure is an MRI procedure performed to identify the fornix of the patient and/or one or more other brain locations. Alternatively or additionally, different patient imaging procedures can be used including imaging procedures selected from the group consisting of X-ray; ultrasound imaging; fMRI; PET scan; and combinations of these. Multiple imaging procedures can be performed, such as similar imaging procedures performed at different times, or different imaging procedures performed at the same or different times. In one embodiment, a first imaging procedure is performed at least 7 days prior to a second imaging procedure. In another preferred embodiment, a first imaging procedure is an MRI procedure and a second imaging procedure is selected from the group consisting of: a second MRI procedure; an X-ray; an ultrasound imaging procedure; an fMRI; a PET scan; and combinations of these. Multiple patient images, collected in one or more similar or dissimilar imaging procedures, can be collected. These images can be used in combination, in comparison, or both. In some embodiments, the two procedures are performed at different times and one or more patient parameters are compared, such as parameters selected from the group consisting of: brain size; brain shape; and brain thickness. In some embodiments, an amyloid PET scan can be used to assess the presence of amyloid in a patient. In some embodiments, a resting state BOLD fMRI sequence is performed to evaluate Default Mode Network or other brain state. In some embodiments, Diffusion Tensor Imaging and tractography are performed, such as to create an image of microstructures of the brain to assess white matter abnormalities (e.g. of the fornix).

Figure 4:
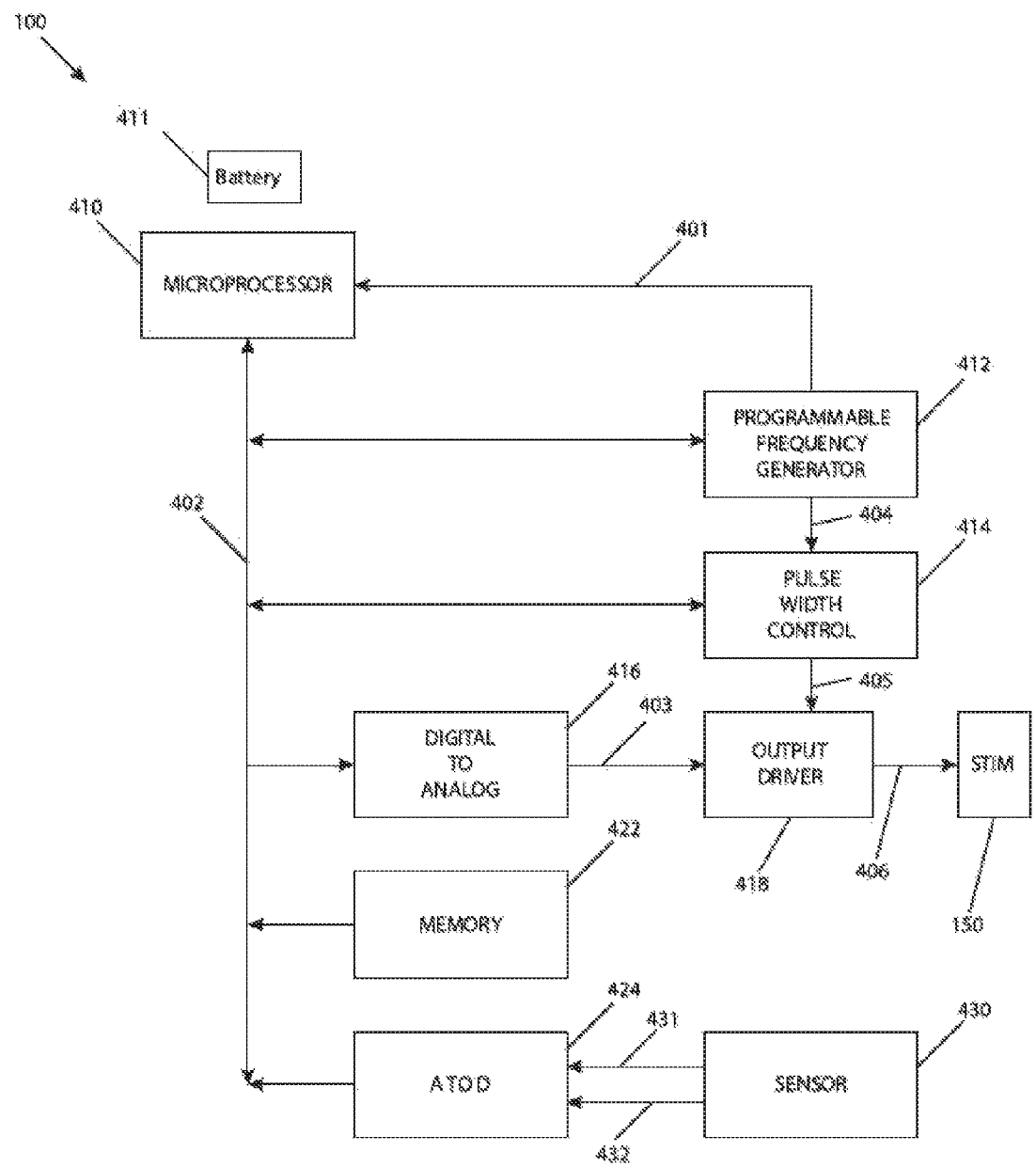
FIG. 4 illustrates a schematic of an electrical brain stimulator, consistent with the present inventive concepts.

In STEP 530, at least a portion of a brain stimulator can be implanted, such as an implantation of one or more portions of brain stimulator 100 described in reference to FIG. 1 hereabove and/or stimulator 100 described in reference to FIG. 4 herebelow. The one or more implantable portions of brain stimulator 100 can be implanted in one or more surgeries. The surgery can include implantation of a lead comprising one or more electrodes, such as one or more electrodes to be positioned proximate the fornix of the patient's brain B. One or more stimulating elements such as electrodes can be implanted in a location selected from the group consisting of: in the Papez Circuit of the patient's brain; approximately 2 mm anterior and parallel to the vertical portion of the fornix; in the optic tract such that the ventral-most contact is 2 mm above the dorsal surface of the optic tract; approximately 5 mm from the midline; and combinations of these. A post-operative imaging procedure such as an MRI can be performed to assess and/or confirm position of one or more implanted electrodes or other components of the system, such as to confirm location of multiple electrodes relative to the fornix or other target location within the patient's brain. The diagnostic tool can be an imaging device, and the diagnostic data can include one or more images produced by the diagnostic device used to select one or more electrodes or other stimulating elements configured to receive stimulation energy. The one or more stimulating elements can be selected based on their proximity and/or relative position to a stimulation target, such as the fornix. For example a first electrode providing stimulating energy generating a first set of diagnostic data can be selected over a second electrode providing stimulating energy and generating a second set of similar diagnostic data (e.g. similar therapeutic benefit) based on information provided by an imaging device (e.g. when the first electrode is in a more desirable position relative to a stimulation target than the second electrode). In some embodiments, electrode selection is made based on image data to prevent stimulation on non-target tissue (i.e. tissue whose stimulation is to be avoided or at least reduced).

In alternative embodiments, brain stimulation is provided by an external, non-invasive stimulation device (i.e. one or more fully non-implanted stimulation system components). In embodiments including an implanted stimulator or a stimulator including at least an implanted portion, at least one stimulation element can be implanted in, on or near the brain of a patient. The at least one stimulation element of the stimulator can be positioned in, on or near the brain of the patient based on the at least one patient image. The at least one stimulation element can be placed via a visual analysis of the at least one image, and/or one or more mathematical or other computational analysis or analyses of the patient image. In some embodiments, the at least one stimulation element is positioned in and/or proximate the fornix of the patient's brain, as has been described in hereabove. In another embodiment, the at least one stimulation element, such as a stimulation element comprising at least two electrodes, is positioned to provide bipolar stimulation of the fornix or other brain tissue. The at least one stimulation element can comprise at least one electrode configured to deliver electrical energy. Proper positioning of the stimulation element can be confirmed after placement, such as with a subsequent MRI or other patient image.

The stimulation element, such as one or more stimulation elements 150 of stimulator 100 of FIG. 1, can comprise an electrical stimulation element such as an electrode or a magnet such as an electromagnet. Alternatively or additionally, the stimulation element can comprise an optical stimulation element, such as a visible light element; an infrared light element; and combinations of these. Alternatively or additionally, the stimulation element can comprise a chemical stimulation element, such as a drug or other agent delivery assembly. The drug delivery assembly can be configured to deliver one or more of: biologically active molecules; neurotransmitters; and neurotrophic factors. The stimulation element can deliver one or more drugs or pharmaceutical agents, and delivery rate or drug concentration can be determined based on patient tolerance, such as a tolerance determined in a titration procedure performed using diagnostic tool 300 of FIG. 1. In a particular embodiment, the stimulation element is constructed and arranged to deliver a cholinesterase inhibitor. In another particular embodiment, an electrode and a second stimulation element is included. The second stimulation element can comprise an element selected from the group consisting of: a second electrode; a magnet; an optical element; a chemical or other agent delivery assembly; and combinations of these.

In STEP 540, one more diagnostic tests can be performed, such as using diagnostic tool 300 of FIG. 1 to gather diagnostic data 305, as described hereabove. The diagnostic data collected can be collected during stimulation with one or more test stimulation parameters, such as test stimulation parameters 106 described hereabove. Diagnostic tool 300 can be used to reposition one or more stimulation elements, such as a repositioning performed during the implantation procedure or during a subsequent surgical or minimally invasive procedure. This repositioning can be based on maximizing a desirable patient effect, such as maximizing recalled memory or memories. Alternatively or additionally, the repositioning can be based on minimizing an adverse event, such as to minimize chest pain; undesired EKG signal or signals; undesired EEG signal or signals; labored breathing; twitching; undesired heart rate; undesired blood pressure; and combinations of these. Alternatively or additionally, the repositioning can be based on minimizing a neurological condition of the patient, such as a level of one or more of: paranoia; psychosis; anxiety; depression; and confusion.

Diagnostic data 305 can be gathered prior to, during or after implantation of one or more portions of the stimulation system, such as diagnostic data gathered at least two weeks after implantation of a stimulator portion. During or after implantation of the implanted stimulator portion, a decision can be made to adjust at least one stimulation parameter based on the diagnostic data 305. The adjusted parameter can be a stimulation parameter selected from the group consisting of: voltage level such as an average voltage level, rms voltage level and/or a peak voltage level; current level such as an average current level, rms current level and/or a peak current level; power level such as an average power level, rms power level and/or a peak power level; frequency of stimulation signal; series of frequencies of the stimulation signal; phase of stimulation signal; pulse width modulation ratio; signal pulse width; current density such as current density applied to tissue; single electrode selected to receive stimulation energy; set of electrodes selected to receive monopolar and/or bipolar stimulation energy; agent delivery rate; physiologic concentration; power of light delivered to tissue; frequency of light delivered to tissue; a modulation parameter of light delivered to tissue; amplitude of sound delivered to tissue; frequency of sound delivered to tissue; a modulation parameter of sound delivered to tissue; mass of agent delivered to tissue; volume of agent delivered to tissue; concentration of agent delivered to tissue; delivery rate of agent delivered to tissue; and combinations of these. Diagnostic data 305 can be used to set initial stimulation parameters and/or to modify existing stimulation parameters.

The implantation procedure can include a calibration or titration procedure, such as procedures which use a diagnostic tool of the present inventive concepts to optimize or otherwise modify one or more stimulation parameters (e.g. one or more test stimulation parameters or treatment stimulation parameters) such as one or more stimulation parameters selected from the group consisting of: an electromagnetic energy delivery parameter such as voltage or current delivered; a magnetic energy delivery parameter such as field strength or field orientation; a light delivery parameter such as wavelength or magnitude of light delivered; a sound delivery parameter such as frequency or amplitude of a delivered sound wave; a chemical delivery parameter such as a concentration of a drug or other agent delivered or a rate of an agent delivered; and combinations of these. If successful calibration or titration cannot be achieved, the implanted stimulator portion can be removed and the procedure abandoned. Alternatively, if a particular adverse event occurs, the implanted stimulator portion can be explanted. Typical adverse events causing explantation can include but are not limited to: chest pain; labored breathing; twitching; unacceptable EKG signal or combination of signals; unacceptable EEG signal or combination of signals; undesired heart rate; undesired blood pressure; and combinations of these. Alternatively or additionally, typical adverse events causing explantation can be an unacceptable neurological state such as an unacceptable level of one or more of: paranoia; psychosis; anxiety; depression; and confusion.

STEP 540 can include multiple diagnostic tests performed by one or more diagnostic tools of the present inventive concepts, such as the one or more diagnostic tools 300 described in reference to FIG. 1 hereabove. The diagnostic procedure can include a series of diagnostic tests performed relatively continuously. The diagnostic procedure can include confirming electrode placement via an impedance measurement, for example during and/or after an implantation step. The diagnostic procedure can include measuring toxicity at one or more patient locations, and a stimulation parameter can be adjusted if a measured toxicity exceeds a threshold. The diagnostic procedure can include a patient memory test that produces results, and a stimulation parameter can be adjusted if the results exceed a threshold. The diagnostic procedure can include a learning task such as a task selected from the group consisting of: a memory task; a cognitive task; a motor task; a standardized test such as a full or partial ADAS-Cog or California Verbal Learning test; and combinations of these. Based on the outcome from any of the above described diagnostic procedures, at least one stimulation parameter can be adjusted (e.g. a test stimulation parameter and/or a treatment stimulation parameter), for example an adjustment of a parameter selected from the group consisting of: voltage level; current level; current density level; a duty cycle parameter such as a pulse width duration; an energy delivery frequency; and combinations of these.

STEP 540 can include sensing a characteristic indicative of the extent of the cognitive disorder and generating a sensor signal and regulating the operation of the stimulator in response to the sensor signal. In some embodiments, sensing a characteristic indicative of the extent of the cognitive disorder and generating a sensor signal can comprise detecting a neurochemical characteristic of the cognitive disorder, for example the signal may represent a neurochemical characteristic selected from the group consisting of: neurotransmitter level, pH concentration, ion concentration, lactate level, cerebral blood flow, glucose utilization, and oxygen extraction. In some embodiments, sensing a characteristic indicative of the extent of the cognitive disorder and generating a sensor signal can comprise detecting an electrophysiological characteristic of the cognitive disorder, for example an electrophysiological characteristic is selected from the group consisting of: the activity of one or more neurons, collectively or singly; local field potentials; event related potentials (ERPs); a characteristic collected by an electroencephalogram; a characteristic collected with MagnetoEncephalography (MEG); a characteristic collected by an electrocorticogram; and combinations of these.

STEP 540 can include sensing a characteristic indicative of the extent of the cognitive disorder, generating a sensor signal, and, if the sensor signal is outside of a predetermined threshold, treating the cognitive disorder by initiating stimulation therapy by the stimulator. STEP 540 can include determining the threshold of one or more stimulation parameters (i.e. the "stimulation threshold" as described herein) associated with an adverse event, such as an adverse event that occurs during continuous or intermittent adjustment of one or more stimulation parameters as described in reference to FIG. 3 herebelow. STEP 540 can include determining the stimulation threshold of one or more stimulation parameters associated with onset of a therapeutic benefit to the patient, such as a recalled memory event or an improved memory test score.

In some embodiments, multiple portions of brain tissue are stimulated sequentially, such as by sequentially stimulating a set of multiple electrodes. For example, a lead comprising a set of multiple electrodes can be sequentially stimulated in order to identify one or more electrodes that avoid an adverse event and/or provide enhanced therapeutic benefit to the patient. In these embodiments, two or more electrodes can be stimulated with bipolar stimulation energy.

STEP 550 comprises setting one or more treatment stimulation parameters (e.g. treatment stimulation parameters 107 of FIG. 1 described hereabove) based on diagnostic data 305 collected during STEP 540 or other diagnostic data collected by a diagnostic tool of the present inventive concepts. In some embodiments, the treatment stimulation parameters approximate one or more test stimulation parameters at which a desirable result was achieved, such as a desired therapeutic benefit. In some embodiments, the treatment stimulation parameters are a safety margin below a level at which a test stimulation parameter resulted in an adverse event, as has been described in detail in reference to FIG. 1 hereabove.

One or more portions of STEP 540 can be performed prior to STEP 520, prior to STEP 530 and/or after STEP 550. STEP 540 can be performed multiple times, such as one or more times prior to STEP 520, one or more times after STEP 520 and before STEP 530, one or more times after STEP 530 and before STEP 550, and/or one or more times after STEP 550. In some embodiments, STEPs 520 and 550 are performed multiple times. In some embodiments, multiple performances of STEP 540 are performed (e.g. multiple productions of diagnostic data 305 at multiple test stimulation parameters 106), and the collective diagnostic data 305 is used to produce a set of treatment stimulation parameters 107 set in a subsequent step 550. In some embodiments, multiple performances of STEP 540 are performed and each result in a STEP 550 being performed in which one or more treatment stimulation parameters 107 are initiated and/or modified.

Figure 3:
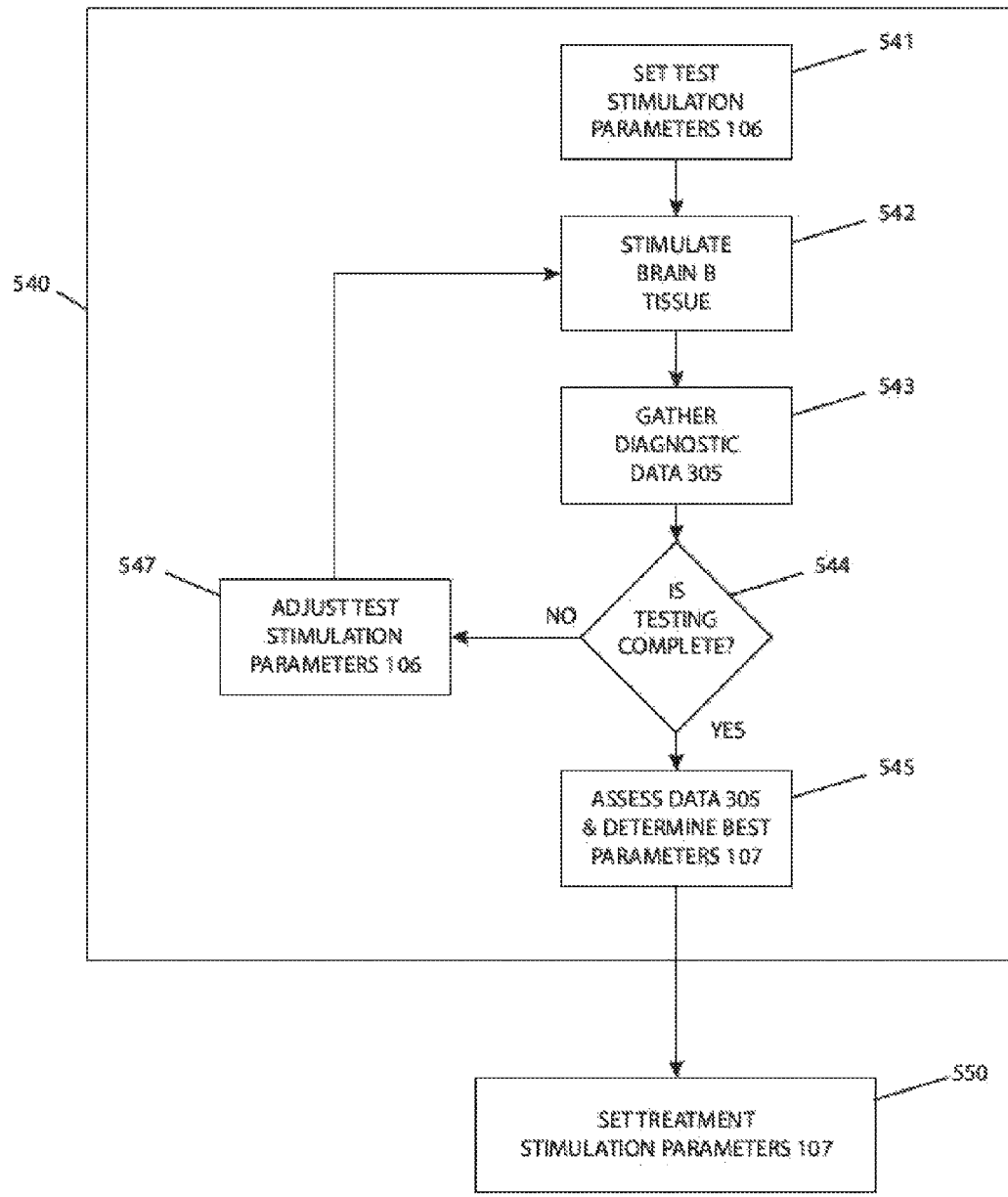
FIG. 3 illustrates a flow chart of a series of steps for performing the diagnostic test of FIG. 2, consistent with the present inventive concepts.

Referring now to FIG. 3, a flow chart of a series of steps for performing STEP 540 of FIG. 2 is illustrated, consistent with the present inventive concepts. STEPs 541 through 546 of FIG. 3 can be performed using one or more components of system 10 of FIG. 1 as described hereabove. In STEP 541, a set of test stimulation parameters 106 are programmed into a stimulation device (e.g. a first set of test stimulation parameters 106' programmed into stimulator 100 using controller 200 as described in reference to FIG. 1). In STEP 542, one or more portions of brain tissue of a patient (e.g. tissue of brain B of FIG. 1) are stimulated using the test stimulation parameters 106. In STEP 543, diagnostic data 305 is gathered with one or more diagnostic tools (e.g. diagnostic data 305 gathered by diagnostic tool 300 of FIG. 1) during stimulation with the test stimulation parameters 106. In STEP 544, a determination of testing completeness is performed. If testing is not complete, STEP 547 is performed in which one or more of the test stimulation parameters 106 are adjusted (e.g. a second set of test stimulation parameters 106" programmed into stimulator 100 using controller 200). Subsequently, STEP 542 is performed again, stimulating brain B tissue with the adjusted test stimulation parameters 106. STEP 543 is also performed again, gathering new diagnostic data 305 at the adjusted test stimulation parameters 106. STEP 544 is performed again, determining test completeness. If test is not complete, STEPs 547, 542, 543 and 544 are continuously repeated until testing is complete.

In some embodiments, repeated stimulation with initial and adjusted test stimulation parameters 106 includes incremental increases or decreases of a test stimulation parameter 106 such a series of increases in stimulation voltage and/or current as described hereabove. In some embodiments, a first test stimulation parameter 106 comprises a voltage level below 3.0 Volts, and a second and subsequent test stimulation parameters 106 comprise values correlating to sequentially increasing the voltage (e.g. in 0.1, 0.2, 0.3, 0.4 or 0.5 Volt increments) until an adverse event and/or a therapeutic benefit is recorded by a diagnostic device of the present inventive concepts. In some embodiments, the test stimulation parameter 106 used does not exceed a maximum, such as a maximum less than or equal to approximately 10.0 Volts, 9.0 Volts, 8.0 Volts or 7.0 volts. In some embodiments, the voltage or other test stimulation parameter 106 level is increased slowly, such as an increment made in time intervals of approximately at least 0.5 seconds, 2.0 seconds, 5.0 seconds, 10.0 seconds or 30.0 seconds.

In some embodiments, a set of test stimulation parameters 106 used in multiple steps 542 include at least one test stimulation parameter 106 in which no stimulation is performed (e.g. a test stimulation parameter 106 of 0.0 Volts). In these embodiments, a therapeutic benefit of stimulation can be confirmed (e.g. by the absence of the benefit when no stimulation was given, such as when the diagnostic device comprises a memory test tool as described herein wherein a higher score is achieved with one set of test stimulation parameters 106).

After testing completeness has been confirmed in STEP 544, STEP 545 is performed in which an assessment of the diagnostic data 305 produced by the one or more diagnostic tools 300 is assessed to determine an optimized set of one or more treatment stimulation parameters to be used to stimulate the brain tissue of the patient.

In STEP 550, the optimized set of treatment stimulation parameters 107 are programmed into the stimulation device, such as is described in reference to STEP 550 of FIG. 2 hereabove. In some embodiments, the treatment stimulation parameters 107 are a safety margin below a level at which a test stimulation parameter 106 resulted in an adverse event, as has been described in detail in reference to FIG. 1 hereabove.

In some embodiments, a first series of STEPs 542 through 547 are performed with a first set of test stimulation parameters 106 during a first time period to gather a first set of diagnostic data 305 with a diagnostic tool 300 of the present inventive concepts, and a second series of STEPs 542 through 547 are performed with a second set of test stimulation parameters 106 during a second time period to gather a second set of diagnostic data 305. The treatment stimulation parameters 107 can be based on the first set of test stimulation parameters 106 and/or the second set of test stimulation parameters 106, such as when the chosen set of treatment stimulation parameters 107 avoids an adverse event and/or causes a therapeutic benefit to the patient or other desired event. Accordingly, a third and additional set of test stimulation parameters 106 can be delivered in a third and additional time periods. The various time periods can be similar or dissimilar in length of time. In some embodiments, one or more time periods comprise a length of time less than 24 hours, such as less than 6 hours, less than 3 hours, less than 1 hour, less than 30 minutes, less than 15 minutes, less than 10 minutes, less than 5 minutes or less than 2 minutes. Any or all of the test stimulation parameters 106 can be based on diagnostic data 305 gathered by a diagnostic tool 300 of the present inventive concepts during a previous test or treatment stimulation.

Referring now to FIG. 4, a schematic view of an electrical stimulation device is illustrated, consistent with the present inventive concepts. Stimulation device 100 delivers electrical stimulation energy including a stimulus pulse frequency that is controlled by programming a value to a frequency generator 412 (e.g. a programmable frequency generator) using bus 402. The frequency generator 412 provides an interrupt signal to microprocessor 410 through an interrupt line 401 when each stimulus pulse is to be generated. The programmable frequency generator 412 communicates with a pulse width control module 414 via pathway 404. The frequency generator 412 can be implemented by a commercial device model CDP1878 sold by Harris Corporation. The amplitude for each stimulus pulse is programmed to a digital to analog converter 416 using bus 402. The analog output is conveyed through a conductor 403 to an output driver circuit 418 to control stimulus amplitude.

Microprocessor 410 also programs pulse width control module 414 using bus 402. The pulse width control module 414 provides an enabling pulse of duration equal to the pulse width via a conductor 405. Pulses with the selected characteristics are then delivered from stimulation device 100 through cable 406 to stimulation element 150. Stimulation element 150, typically comprising one or more electrodes as are described hereabove, can be positioned to stimulate the fornix and/or other regions of the brain or other body tissue. At the time that all or a portion of stimulation device 100 is implanted or otherwise positioned, a clinician can program certain key parameters into the memory 422 of stimulation device 100, such as via telemetry from an external controller, such as controller 200 described in reference to FIG. 1 hereabove. These parameters can be updated subsequently as needed, such as to modify one or more test or treatment stimulation parameters based on diagnostic data produced by a diagnostic device (e.g. diagnostic data 305 produced by diagnostic tool 300 of FIG. 1). Battery 411 can provide electrical power to one or more components of stimulation device 100 described herein.

Stimulation element 150 can comprise one or more deep brain stimulation electrodes, such as electrodes model 3387 produced by Medtronic of Minneapolis, Minn. These electrodes can be bilaterally implanted such that the tips of the electrodes are positioned in a region where cells can be recorded during micro-recording mapping. Alternatively, a single electrode can be implanted unilaterally. Energy can be applied at a frequency of 2 Hz to 1000 Hz, such as at a frequency of approximately 130 Hz. Energy can be delivered at a constant or varied pulse amplitude, such as at a constant pulse amplitude of approximately 500 µA. Energy can be delivered at a voltage between 0.1 and 10 Volts, such as between 1 Volt and 6 Volts, such as at a voltage of approximately 3 Volts. Energy delivery can be given in a series of on and off times, such as with an on-time of approximately 30 µseconds to 200 µseconds, such as with an on time of approximately 90 µseconds. The duration of energy delivery can range from 30 minutes to 120 minutes, such as a duration of approximately 60 minutes, which can be repeated at regular or irregular time intervals.

The embodiments of the present inventive concepts can be configured as open-loop systems. The microcomputer algorithm programmed by the clinician sets the stimulation parameters of the stimulation device 100. In open-loop embodiments, this algorithm can change one or more parameter values over time, but does so independent of any changes in symptoms or other physiologic changes the patient can be experiencing. Alternatively, a closed-loop system discussed below which incorporates a sensor 430 to provide feedback can be used to provide enhanced results. Sensor 430 (e.g. an implanted or external sensor) can be used with a closed loop feedback system in order to automatically or semi-automatically determine the level of stimulation necessary to achieve the desired level of improved cognitive function and/or to avoid an adverse event. In closed-loop embodiments, microprocessor 410 can execute an algorithm in order to provide stimulation with closed loop feedback control. Such an algorithm can analyze a sensed signal from sensor 430 and deliver stimulation therapy (e.g. delivery or electrical, magnetic, light, sound and/or chemical treatment therapy) based on the sensed signal. Adjustments can be made to one or more treatment stimulation parameters when the signal falls within or outside predetermined values or windows, for example, predetermined levels of BDNF and other neurotrophins (e.g., NGF, CNTF, FGF, EGF, NT-3) and corticosteroids. Closed loop applications can be driven by diagnostic data, such as diagnostic data 305 produced by diagnostic tool 300 described in reference to FIG. 1 hereabove.

For example, in some embodiments, the patient can engage in a specified cognitive task, wherein the system measures one or more characteristics to determine if the levels sensed by sensor 430 are at expected thresholds. If one or more of the sensed characteristics are outside a predetermined threshold, the system can initiate and/or modify one or more treatment stimulation parameters, such as to enhance or otherwise improve cognitive function.

In some embodiments, the system can be continuously providing closed-loop feedback control. In other embodiments, the system can intermittently operate in closed-loop feedback control, such as based on a time of day (e.g., during hours that the patient is awake) or based on a cognitive task (e.g., when the patient is working). In yet other embodiments, the system can be switchable between open-loop and closed-loop by operator control, automatically and/or manually (e.g. manually via a handheld controller).

In some embodiments, stimulation therapy can be provided in relation to learning a task. For example, electrical stimulation and/or drug delivery can be applied before, after and/or during the performance of a memory, cognitive or motor task to facilitate the acquisition of learning or consolidation of the task. In so doing, the rate of memory acquisition and learning can be accelerated and enhanced in magnitude. For example, electrical stimulation and/or drug delivery can be provided before, during, and/or after periods when the patient is learning a new language or playing a new instrument. Such therapy can be useful during the encoding, consolidation and/or retrieval phases of memory. The neuromodulation intervention, brain stimulation or drug delivery can occur before, after or simultaneously to the memory, cognitive of motor skill task.

In another aspect of the invention, stimulation therapy can be utilized to enhance neurogenesis as a method of improving cognitive function. Techniques for enhancing neurogenesis through treatment therapy are disclosed in U.S. patents "Cognitive Function Within A Human Brain", U.S. Ser. No. 11/303,293; "Inducing Neurogenesis Within A Human Brain", U.S. Ser. No. 11/303,292; and "Regulation of Neurotrophins", U.S. Ser. No. 11/303,619; as well as U.S. patent application "Method Of Treating Cognitive Disorders Using Neuromodulation", U.S. Ser. No. 11/364,977; the contents of which are each incorporated herein by reference in their entirety.

Referring back to FIG. 4, the system can optionally utilize closed-loop feedback control having an analog to digital (A-to-D) converter 424 coupled to sensor 430 via pathways 431 and 432. Output of the A-to-D converter 424 is connected to microprocessor 410 through peripheral bus 402 including address, data and control lines. Microprocessor 410 processes sensor 430 data in different ways depending on the type of transducer in use and regulates delivery, via a control algorithm, of stimulation based on the sensed signal. For example, when the signal on sensor 430 exceeds a level programmed by the clinician and stored in a memory 422, increasing amounts of stimulation can be applied through an output driver circuit 418. In the case of electrical stimulation, a parameter of the stimulation can be adjusted such as amplitude, pulse width and/or frequency.

Parameters which can be sensed include the activity of single neurons as detected with microelectrode recording techniques, local field potentials (LFPs), and event related potentials (ERPs), for example in response to a memory task or sensory stimulus and electroencephalogram or electrocorticogram. For example, U.S. Pat. No. 6,227,203 provides examples of various types of sensors that can be used to detect a symptom or a condition of a cognitive disorder and responsively generate a neurological signal. In an embodiment, a neurochemical characteristic of the cognitive function can be sensed, additionally or alternatively. For example, sensing of local levels of neurotransmitters (e.g. glutamate, GABA, Aspartate), local pH or ion concentration, lactate levels, local cerebral blood flow, glucose utilization or oxygen extraction can also be used as the input component of a closed loop system. These measures can be taken at rest or in response to a specific memory or cognitive task or in response to a specific sensory or motor stimulus. In another embodiment, an electro-physiological characteristic of the cognitive function can be sensed by sensor 430. The information contained within the neuronal firing spike train, including spike amplitude, frequency of action potentials, signal to noise ratio, the spatial and temporal features and the pattern of neuronal firing, oscillation behavior and inter-neuronal correlated activity can be used to deliver therapies on a contingency basis in a closed loop system. Moreover, treatment therapy delivered can be immediate or delayed, diurnal, constant or intermittent depending on contingencies as defined by the closed loop system.

The foregoing description and accompanying drawings set forth a number of examples of representative embodiments at the present time. Various modifications, additions and alternative designs will become apparent to those skilled in the art in light of the foregoing teachings without departing from the spirit hereof, or exceeding the scope hereof, which is indicated by the following claims rather than by the foregoing description. All changes and variations that fall within the meaning and range of equivalency of the claims are to be embraced within their scope.

What is claimed is:
1. A system for treating a patient comprising:
a stimulator for stimulating brain tissue;
a controller for setting stimulation parameters comprising at least one test stimulation parameter of the stimulator and at least one treatment stimulation parameter of the stimulator; and
a diagnostic tool for measuring at least one patient parameter and producing diagnostic data representing the at least one measured patient parameter;
wherein the controller is configured to analyze the diagnostic data and compare the diagnostic data to a threshold characteristic of an adverse event or a desired event;
wherein the stimulator is constructed and arranged to deliver test stimulation energy to the brain tissue based on the at least one test stimulation parameter and to deliver treatment stimulation energy to the brain tissue based on the at least one treatment stimulation parameter;
wherein the at least one treatment stimulator parameter is determined based on the diagnostic data;
wherein the controller is configured to set the at least one treatment stimulation parameter based on a safety margin based on the comparison of the diagnostic data to the threshold characteristic; and
wherein the system is constructed and arranged to treat at least one of a neurological disease or a neurological disorder.

2. The system according to claim 1, wherein the at last one of a neurological disease or a neurological disorder comprises Alzheimer's Disease.

3. The system according to claim 1, wherein the brain tissue stimulated comprises a fornix.

4. The system according to claim 1, wherein the system is constructed and arranged to determine the at least one treatment stimulation parameter to at least one of prevent or reduce the adverse event.

5. The system according to claim 1, wherein the system is constructed and arranged to determine the at least one treatment stimulation parameter to improve treatment of the at least one of a neurological disease or a neurological disorder.

6. The system according to claim 1, wherein at least one of the stimulation parameters comprises a signal voltage ranging between 0.1 Volts and 10.0 Volts.

7. The system according to claim 1, wherein the controller is constructed and arranged to set at least one stimulation parameter based on a threshold at which the adverse event is detected by the diagnostic tool.

8. The system according to claim 7, wherein the adverse event comprises an event selected from the group consisting of: undesirable heart rate; undesirable respiration rate; undesirable sweating; undesirable hallucinations; undesirable tingling; flushing; an undesirable psychiatric effect; an undesirable cognitive effect; unpleasant generalized warming; undesirable perceptions described as déjà vu; seizure; synchronized neuronal firing pattern; undesired neural response time; undesired brain state; undesired theta phase; undesired p300 amplitude; and combinations thereof.

9. The system according to claim 7, wherein the at least one stimulation parameter is set using the safety margin.

10. The system according to claim 9, wherein the safety margin comprises at least a 10% safety margin.

11. The system according to claim 1, wherein the controller is constructed and arranged to set at least one stimulation parameter based on a threshold at which a desired event was detected by the diagnostic tool.

12. The system according to claim 11, wherein the desired event comprises an event selected from the group consisting of: recall of a desired memory; achievement of desired memory learning; desired level of neuronal activity; acceptable physiologic condition such as an acceptable heart rate or acceptable level of neuronal activity; experiential phenomena; and combinations thereof.

13. The system according to claim 1, wherein the diagnostic tool is constructed and arranged to detect an adverse event.

14. The system according to claim 13, wherein the adverse event comprises an event selected from the group consisting of: undesirable heart rate; undesirable respiration rate; undesirable sweating; undesirable hallucinations; undesirable tingling; flushing; undesirable psychiatric effect; undesirable cognitive effect; unpleasant generalized warming; undesirable perceptions described as déjà vu; seizure; synchronized neuronal firing pattern; undesired neural response time; undesired brain state; undesired theta phase; undesired p300 amplitude; and combinations thereof.

15. The system according to claim 1, wherein the diagnostic tool comprises a device selected from the group consisting of: heart rate monitor; EKG measurement device; oximeter; combined heart rate and oximeter device such as a pulse oximeter; blood pressure measurement device; neuronal activity measurement device; EEG measurement device; evoked response potential (ERP) measurement device; neurochemical analysis device; memory test device; memory test form; respiration measurement device; sweat measurement device; skin conductivity measurement device; pH measurement device; body motion measurement device; imaging device; and combinations thereof.

16. The system according to claim 1, wherein the diagnostic tool comprises at least two devices selected from the group consisting of: heart rate monitor; EKG measurement device; oximeter; combined heart rate and oximeter device such as a pulse oximeter; blood pressure measurement device; neuronal activity measurement device; EEG measurement device; evoked response potential (ERP) measurement device; neurochemical analysis device; memory test device; memory test form; respiration measurement device; sweat measurement device; skin conductivity measurement device; pH measurement device; body motion measurement device; imaging device; and combinations thereof.

17. The system according to claim 1, wherein the diagnostic tool comprises at least a heart rate monitor and a blood pressure measurement device.

18. The system according to claim 1, wherein the diagnostic tool comprises at least one of a heart rate monitor or a blood pressure measurement device.

* * * * *